US006458533B1

(12) United States Patent
Felder et al.

(10) Patent No.: US 6,458,533 B1
(45) Date of Patent: Oct. 1, 2002

(54) HIGH THROUGHPUT ASSAY SYSTEM FOR MONITORING ESTS

(75) Inventors: Stephen Felder; Bruce Seligmann; Richard M. Kris, all of Tucson, AZ (US)

(73) Assignee: High Throughput Genomics, Inc., Tucson, AZ (US)

( * ) Notice: Subject to any disclaimer, the term of this patent is extended or adjusted under 35 U.S.C. 154(b) by 0 days.

(21) Appl. No.: 09/218,089

(22) Filed: Dec. 22, 1998

Related U.S. Application Data

(63) Continuation-in-part of application No. 09/109,076, filed on Jul. 2, 1998, now Pat. No. 6,232,066.
(60) Provisional application No. 60/068,291, filed on Dec. 19, 1997, now abandoned.

(51) Int. Cl.[7] ................. C12Q 1/68; C12P 19/34; C07H 21/02; C07H 21/04
(52) U.S. Cl. ................. 435/6; 435/91.1; 435/91.2; 536/232; 536/24.3
(58) Field of Search .................. 435/6, 91.2; 536/23.3, 536/24.3

(56) References Cited

U.S. PATENT DOCUMENTS

| | | | |
|---|---|---|---|
| 4,228,237 A | 10/1980 | Hevey et al. | 435/7 |
| 4,563,419 A | 1/1986 | Ranki et al. | 435/6 |
| 4,716,106 A | 12/1987 | Chiswell | 435/6 |
| 4,751,177 A | 6/1988 | Stabinsky | 435/6 |
| 4,868,105 A | 9/1989 | Urdea et al. | 435/6 |
| 4,925,785 A | 5/1990 | Wang et al. | 435/6 |
| 4,994,373 A | 2/1991 | Stavrianopoulos et al. | 435/6 |
| 5,143,854 A | 9/1992 | Pirrung et al. | 436/518 |
| 5,172,270 A * | 12/1992 | Nilsen et al. | 536/27 |
| 5,288,609 A | 2/1994 | Engelhardt et al. | 435/6 |
| 5,324,633 A | 6/1994 | Fodor et al. | 435/6 |
| 5,374,524 A | 12/1994 | Miller | 435/6 |
| 5,482,867 A | 1/1996 | Barrett et al. | 436/518 |
| 5,510,270 A | 4/1996 | Fodor et al. | 436/518 |
| 5,545,531 A | 8/1996 | Rava et al. | 435/6 |
| 5,547,839 A | 8/1996 | Dower et al. | 435/6 |
| 5,556,748 A | 9/1996 | Douglas | 435/6 |
| 5,605,798 A | 2/1997 | Köster | 435/6 |
| 5,643,730 A | 7/1997 | Banker et al. | 435/6 |
| 5,661,028 A | 8/1997 | Foote | 435/287.2 |
| 5,744,305 A | 4/1998 | Fodor et al. | 435/6 |
| 5,770,370 A | 6/1998 | Kumar | 435/6 |
| 5,789,165 A | 8/1998 | Oku et al. | 435/6 |
| 6,083,763 A | 7/2000 | Balch | |
| 6,238,869 B1 * | 5/2001 | Kris et al. | 435/6 |

FOREIGN PATENT DOCUMENTS

| | | |
|---|---|---|
| DE | 19518217 | 11/1995 |
| EP | 0698792 | 2/1996 |
| EP | 0742286 | 11/1996 |
| EP | 0 742 286 A2 | 11/1996 |
| EP | 0 846 776 A | 6/1998 |
| WO | 89/11548 | 11/1989 |
| WO | WO 93 25563 | 12/1993 |
| WO | 97/05277 | 2/1997 |
| WO | 97/07245 | 2/1997 |
| WO | 97/27317 | 7/1997 |
| WO | 9727317 | 7/1997 |
| WO | 9731256 | 8/1997 |
| WO | WO 99 28494 A | 6/1999 |

OTHER PUBLICATIONS

Pease et al., "Light–generated oligonucleotide arrays for rapid DNA sequence analysis" Proc. Natl. Acad. Sci USA vol. 91, pp. 5022–5026, 1994.*

Scholler et al.: "Fine–mapping of shotgun template libraries; an efficient strategy for the systematic sequencing of genomic DNA" *Nucleic Acid Research*, GB, Oxford University Press, Surry, vol. 23, No. 19, 1995, pp. 3842–3849.

Lehrach H et al.; "Hybridization fingerprinting in genome mapping and sequencing" *Genome Analysis*, US, Cold Spring Harbor Lab. Press, vol. 1, 1990, pp. 39–81.

Labat I et al.: "Simulations of ordering and sequence reconstruction of random DNA clones hybridized with a small number of oligomeric probes" *International Conference on Bioinformatics*, XX, XX, 1993, pp. 555–565.

Maier et al. (1997). Drug Discovery Today, vol. 2 (8). pp. 315–324.

Kowalak, J., et al. "Posttrascriptional Modification of the Central Loop of Domain V in *Escherichia coli* 23 S Ribosomal RNA", *The Journal of Biological Chemistry*, vol. 270, No. 30, Jul. 28, 1995, pp. 17758–17764.

(List continued on next page.)

*Primary Examiner*—John S. Brusca
*Assistant Examiner*—Young Kim
(74) *Attorney, Agent, or Firm*—Millen, White, Zelano & Branigan, P.C.

(57) ABSTRACT

The present invention relates to compositions, apparatus and methods useful for concurrently performing multiple, high throughput, biological or chemical assays, using repeated arrays of probes. A combination of the invention comprises a surface, which comprises a plurality of test regions, at least two of which, and in a preferred embodiment, at least twenty of which, are substantially identical, wherein each of the test regions comprises an array of generic anchor molecules. The anchors are associated with bifunctional linker molecules, each containing a portion which is specific for at least one of the anchors and a portion which is a probe specific for a target of interest. The resulting array of probes is used to analyze the presence or test the activity of one or more target molecules which specifically interact with the probes. In one embodiment of the invention, the test regions (which can be wells) are further subdivided into smaller subregions (indentations, or dimples).

In one embodiment of the invention, ESTs are mapped. In another embodiment, the presence of a target nucleic acid is detected by protecting the target against nuclease digestion with a polynucleotide fragment, and analyzing the protected polynucleotide by mass spectrometry.

12 Claims, 19 Drawing Sheets

OTHER PUBLICATIONS

Gautheret, D., et al., "Alternate Polyadenylation in Human mRNAs: A Large–Scale Analysis by EST Clustering", *Genome Research,* vol. 8, 1998, pp. 524–530.

Sapolsky, R., et al. "Mapping Genomic Library Clones Using Oligonucleotide Arrays", *Genomics,* vol. 33, 1996, pp. 445–456.

Alper, "Weighing DNA for Fast Genetic Diagnosis", *Science,* vol. 279, Mar. 27, 1998, pp. 2044–2045.

Anderson et al., "Polynucleotide Arrays for Genetic Sequence Analysis", *Topics in Current Chemistry,* vol. 194, 1998, pp. 118–129.

Beattie et al., "Advances in Genosensor Research", *Clinical Chemistry,* vol. 41, No. 5, 1995, pp. 700–706.

Chee et al., "Accessing Genetic Information with High–Density DNA Arrays", *Science,* vol. 274, Oct. 25, 1996, pp. 610–614.

Chetverin et al., "Olignucleotide Arrays: New Concepts and Possibilities", *Bio/Technology,* vol. 12, Nov. 12, 1994, pp. 1093–1099.

DeRisi et al., "Use of a cDNA Microarray to Analyse Gene Expression Patterns in Human Cancer", *Nature Genetics,* vol. 14, Dec. 1996, pp. 457–460.

Eggers et al., "A Microchip for Quantitative Detection . . . ", *BioTechniques,* vol. 17, No. 3 (1994), pp. 516–524.

Eggers et al., "A Review of Microfabricated Devices for Gene–Based Diagnostics", *Hematologic Pathology* 9(1), 1–15 (1995).

Gautheret et al., "Alternate Polyadenylation in Human nRNAs . . . ", *Genome Research,* 8:524–530 (1998).

Maskos et al., "A Novel Method for the Parallel Analysis of Multiple Mutations in Multiple Samples", *Nucleic Acids Research,* 1993, vol. 21, No. 9, pp. 2269–2270.

Hoheisel, "Oligomer–chip Technology", *BioTechnology TIBTECH,* Nov. 1997, vol. 15, No. 1 (166), pp. 465–469.

Lipshutz et al., "Using Oligonucleotide Probe Arrays to Access Genetic Diversity", *BioTechniques,* vol. 19, No. 3 (1995), pp. 442–447.

Lockhart et al., "Expression Monitoring by Hybridization to High–Density Oligonucleotide Arrays", *Nature Biotechnology,* vol. 14, Dec. 1996, pp. 1675–1680.

Marshall et al., "DNA chips: An array of possibilities", *Nature Biotechnology,* vol. 16, Jan. 1998, pp. 27–31.

Niemeyer et al., "Oligonucleotide–directed self–assembly of proteins . . . ", *Nucleic Acids Research,* 1994, vol. 22, No. 25, pp. 5530–5539.

O'Donnell–Maloney et al., "The Development of Microfabricated Arrays for DNA Sequencing and Analysis", *TIBTECH,* vol. 14, Oct. 1996.

Sapolsky et al., "Mapping Genomic Library Clones Using Oligonucleotide Arrays", *Genomics,* 33, 445–456 (1996).

Schullek et al., "A High–Density Screening Format for Encoded Combinatorial Libraries . . . ", *Analytical Biochemistry,* 246, 20–29 (1997).

Shoemaker et al., "Quantitative Phenotype Analysis of Yeast Deletion . . . ", *Nature Genetics,* vol. 14, Dec. 1996, pp. 450–456.

Shuber et al., "High Throughput Parallel Analysis of Hundreds of Patient Samples . . . ", *Human Molecular Genetics,* 1997, vol. 6, No. 3, pp. 337–347.

Southern, "DNA chips; analysing sequence by hybridization . . . ", *Trends in Genetics,* vol. 12, 1996.

Southern, "High–density gridding: techniques and applications", *Current Opinion in Biotechnology,* vol. 7, No. 1, Feb. 1996, pp. 85–88.

Kowalak et al., "Posttrascriptional Modification of the Central Loop of Domain V . . . ", *The Journal of Biological Chemistry,* vol. 270, No. 30, Issue of Jul. 28, pp. 17758–17765, 1995.

\* cited by examiner

SEQUENCE LISTING

```
<160> NUMBER OF SEQ ID NOS:  32

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: anchor

<400> SEQUENCE: 1
tccacgtgag gaccggacgg cgtcc                                          25

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: linker

<400> SEQUENCE: 2
gtcgtttcca tctttgcagt cataggatac tgagtggacg ccgtccggtc ctcacgtgga    60

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: RNA mimic
      (mouse C-jun)

<400> SEQUENCE: 3
ctatgactgc aaagatggaa acgacgatac tgagttggac ctaacattcg atctcattca    60

<210> SEQ ID NO 4
<211> LENGTH: 25
<212> TYPE: DNA
<213> ORGANISM: Artificial Sequence
```

```
<220> FEATURE:
<223> OTHER INFORMATION: Description of Artificial Sequence: detector
      oligonucleotide

<400> SEQUENCE: 4
tgaatgagat cgaatgttag gtcca                                          25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: anchor

<400> SEQUENCE: 5
cactacggct gagcacgtgc gctgc                                          25

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: linker

<400> SEQUENCE: 6
ctaggctgaa gtgtggctgg agtctgcagc gcacgtgctc agccgtagtg               50

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: RNA mimic
      (mouse MIP-2)

<400> SEQUENCE: 7
agactccagc cacacttcag cctaggatac tgagtctgaa caaaggcaag gctaactgac    60

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: detector
      oligonucleotide

<400> SEQUENCE: 8
gtcagttagc cttgcctttg ttcag                                          25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: anchor

<400> SEQUENCE: 9
gtcagttagc cttgcctttg ttcag                                          25

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: linker

<400> SEQUENCE: 10
```

```
accatgtagt tgaggtcaat gaagggcgct cccacaacgc tcgaccggcg          50

<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence: RNA mimic
      (mouse GAPDH)

<400> SEQUENCE: 11
ccttcattga cctcaactac atggtgatac tgagtggaga aacctgccaa gtatgatgac     60

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: detector
      oligonucleotide

<400> SEQUENCE: 12
gtcatcatac ttggcaggtt tctcc                                          25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: anchor

<400> SEQUENCE: 13
gaaccgctcg cgtgttctac agcca                                          25

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: linker

<400> SEQUENCE: 14
ctaccgagca aactggaaat gaaattggct gtagaacacg cgagcggttc               50

<210> SEQ ID NO 15
<211> LENGTH: 60
<212> TYPE: DNA
<213> ORGANISM: Artificial Sequence
<220> FEATURE:
<223> OTHER INFORMATION: Description of Artificial Sequence: RNA mimic
      (mouse L32 protein)

<400> SEQUENCE: 15
atttcatttc cagtttgctc ggtaggatac tgagtgagtc accaatccca acgccaggct    60

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: detector
      oligonucleotide

<400> SEQUENCE: 16
agcctggcgt tgggattggt gactc                                          25
```

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: anchor

<400> SEQUENCE: 17
ctcgttccgc gtccgtggct gccag                                     25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: linker

<400> SEQUENCE: 18
ctggcagcca cggacgcgga acgag                                     25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: anchor

<400> SEQUENCE: 19
cggtcggcat ggtaccacag tccgc                                     25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: linker

<400> SEQUENCE: 20
gcggactgtg gtaccatgcc gaccg                                     25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: anchor

<400> SEQUENCE: 21
gcgcgccgcg ttatgcatct cttcg                                     25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: linker

<400> SEQUENCE: 22
cgaagagatg cataacgcgg cgccg                                     25

<210> SEQ ID NO 23
<211> LENGTH: 70
<212> TYPE: DNA
<213> ORGANISM: murine sp.

<400> SEQUENCE: 23

```
cgagaaatat gacaactcac tcaagattgt cagcaatgca tcctgcacca ccaactgctt      60
gcttgtctaa                                                             70

<210> SEQ ID NO 24
<211> LENGTH: 60
<212> TYPE: DNA
<213> ORGANISM: murine sp.

<400> SEQUENCE: 24
cgagaaatat gacaactcac tcaagattgt cagcaatgca tcctgcacca ccaactgctt      60

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: anchor

<400> SEQUENCE: 25
cgccggtcga gcgttgtggg agcgc                                            25

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: linker

<400> SEQUENCE: 26
cttgagtgag ttgtcatatt tctcggatac tgagtgcgct cccacaacgc tcgaccggcg      60

<210> SEQ ID NO 27
<211> LENGTH: 70
<212> TYPE: DNA
<213> ORGANISM: Artificial Sequence
<220> FEATURE:
<223> OTHER INFORMATION: Description of Artificial Sequence: protection
      fragment (complementary to mouse antisense
      mRNA for GAPDH)

<400> SEQUENCE: 27
cgagaaatat gacaactcac tcaagattgt cagcaatgca tcctgcacca ccaactgctt      60
gcttgtctaa                                                             70

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: detector
      oligonucleotide

<400> SEQUENCE: 28
aagcagttgg tggtgcagga tgcat                                            25

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence: linker

<400> SEQUENCE: 29
atgcatcctg caccaccaac tgcttgatac tgagtgcgct cccacaacgc tcgaccggcg      60
```

-continued

```
<210> SEQ ID NO 30
<211> LENGTH: 70
<212> TYPE: DNA
<213> ORGANISM: Artificial Sequence
<220> FEATURE:
<223> OTHER INFORMATION: Description of Artificial Sequence: protection
      fragment (complementary to mouse antisense
      mRNA for GAPDH)

<400> SEQUENCE: 30
aagcagttgg tggtgcagga tgcattgctg acaatcttga gtgagttgtc atatttctcg    60
gcttgtctaa                                                           70

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: detector
      oligonucleotide

<400> SEQUENCE: 31
cgagaaatat gacaactcac tcaag                                          25

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence:
      phosphorylated peptide
<223> OTHER INFORMATION: Xaa at position 6 is a phosphotyrosine

<400> SEQUENCE: 32

Thr Ser Glu Pro Gln Xaa Gln Pro Gly Glu Asn Leu
 1               5                  10
```

HIGH THROUGHPUT ASSAY SYSTEM FOR MONITORING ESTS

This application claims the benefit of provisional application 60/068,291, filed Dec. 19, 1997, now abandoned, and of U.S. application of Ser. No. 09/109,076, which is a continuation-in-part, filed on Jul. 2, 1998, now U.S. Pat. No. 6,232,066, each of which disclosure is incorporated by reference herein.

BACKGROUND OF THE INVENTION

This invention relates, e.g., to compositions, apparatus and methods useful for concurrently performing multiple biological or chemical assays, using repeated arrays of probes. A plurality of regions each contains an array of generic anchor molecules. The anchors are associated with bifunctional linker molecules, each containing a portion which is specific for at least one of the anchors and a portion which is a probe specific for a target of interest. The resulting array of probes is used to analyze the presence of one or more target molecules which interact specifically with the probes. The invention relates to diverse fields distinguished by the nature of the molecular interaction, including but not limited to pharmaceutical drug discovery, molecular biology, biochemistry, pharmacology and medical diagnostic technology.

Pluralities of molecular probes arranged on surfaces or "chips" have been used in a variety of biological and chemical assays. Assays are performed to determine if target molecules of interest interact with any of the probes. After exposing the probes to target molecules under selected test conditions, detection devices determine whether a target molecule has interacted with a given probe.

These systems are useful in a variety of screening procedures for obtaining information about either the probes or the target molecules. For example, they have been used to screen for peptides or potential drugs which bind to a receptor of interest, among others; to screen samples for the presence of, for example, genetic mutations, allelic variants in a population, or a particular pathogen or strain of pathogen, among many others; to study gene expression, for example to identify the mRNAs whose expression is correlated with a particular physiological condition, developmental stage, or disease state, etc.

SUMMARY OF THE INVENTION

This invention provides compositions, apparatus and methods for concurrently performing multiple biological or chemical assays, and allows for high throughput analysis of multiple samples—for example, multiple patient samples to be screened in a diagnostic assay, or multiple potential drugs or therapeutic agents to be tested in a method of drug discovery. A combination is provided which is useful for the detection of one or more targets in a sample. This combination comprises a surface comprising a plurality of spatially discrete regions, which can be termed test regions and which can be wells, at least two of which are substantially identical. Each surface comprises at least two, preferably at least twenty or more, e.g., at least about 25, 50, 96, 864, or 1536, etc., of such substantially identical regions. Each test region defines a space for the introduction of a sample containing (or potentially containing) one or more targets and contains a biological or chemical array. (Phrases such as "sample containing a target" or "detecting a target in a sample" are not meant to exclude samples or determinations (detection attempts) where no target is contained or detected.) In a general sense, this invention involves arrays to determine whether a target is contained in a sample irrespective of whether it is or is not detected.) This array comprises generic "anchors," each in association with a bifunctional linker molecule which has a first portion that is specific for the anchor and a second portion that comprises a probe which is specific for at least one of the target(s). The combination of this invention is placed in contact with a sample containing one or more targets, which optionally react with a detector molecule(s), and is then interrogated by a detection device which detects reactions between target molecules and probes in the test regions, thereby generating results of the assay.

The invention provides methods and compositions particularly useful for high throughput biological assays. In especially preferred embodiments, the invention can be used for high throughput screening for drug discovery. For example, a high throughput assay can be run in many (100 for example) 96-well microplates at one time. Each well of a plate can have, e.g., 36 different tests performed in it by using an array of about 36 anchor and linker pairs. That is, 100 plates, with 96 wells per plate, and each with 36 tests per well, can allow for a total of 345,000 tests; for example, each of 9,600 different drug candidates can be tested simultaneously for 36 different parameters or assays. High throughput assays provide much more information for each drug candidate than do assays which test only one parameter at a time. For example, it is possible in a single initial high throughput screening assay to determine whether a drug candidate is selective, specific and/or nontoxic. Non-high throughput methods necessitate extensive follow-up assays to test such parameters for each drug candidate of interest. Several types of high throughput screening assays are described, e.g., in Examples 15–17. The ability to perform simultaneously a wide variety of biological assays and to do very many assays at once (i.e., in very high throughput) are two important advantages of the invention.

In one embodiment, for example, using 96-well DNA Bind plates (Corning Costar) made of polystyrene with a derivatized surface for the attachment of primary amines, such as amino acids or modified oligonucleotides, a collection of 36 different oligonucleotides can be spotted onto the surface of every well of every plate to serve as anchors. The anchors can be covalently attached to the derivatized polystyrene, and the same 36 anchors can be used for all screening assays. For any particular assay, a given set of linkers can be used to program the surface of each well to be specific for as many as 36 different targets or assay types of interest, and different test samples can be applied to each of the 96 wells in each plate. The same set of anchors can be used multiple times to re-program the surface of the wells for other targets and assays of interest, or it can be re-used multiple times with the same set of linkers. This flexibility and reusability represent further advantages of the invention.

One embodiment of the invention is a combination useful for the detection of one or more target(s) in a sample, which comprises, before the addition of said sample,
  a) a surface, comprising multiple spatially discrete regions, at least two of which are substantially identical, each region comprising
  b) at least eight different oligonucleotide anchors, each in association with
  c) a bifunctional linker which has a first portion that is specific for the oligonucleotide anchor, and a second portion that comprises a probe which is specific for said target(s).

Another embodiment of the invention is a combination useful for the detection of one or more target(s) in a sample, which comprises, before the addition of said sample, a) a surface, comprising multiple spatially discrete regions, at least two of which are substantially identical, each region comprising b) at least eight different anchors, each in association with c) a bifunctional linker which has a first portion that is specific for the anchor, and a second portion that comprises a probe which is specific for said target(s).

Another embodiment of the invention is a method for detecting at least one target, which comprises contacting a sample which may comprise the target(s) with a combination as described above, under conditions effective for said target(s) to bind to said combination. Another embodiment is a method for determining an RNA expression pattern, which comprises incubating a sample which comprises as target(s) at least two RNA molecules with a combination as described above, wherein at least one probe of the combination is a nucleic acid (e.g., oligonucleotide) which is specific (i.e. selective) for at least one of the RNA targets, under conditions which are effective for specific hybridization of the RNA target(s) to the probe(s). Another embodiment is a method for identifying an agent (or condition(s)) that modulates an RNA expression pattern, which is the method described above for determining an RNA expression pattern, further comprising comparing the RNA expression pattern produced in the presence of said agent (or condition (s)) to the RNA expression pattern produced under a different set of conditions.

By way of example, FIGS. 1 and 2 illustrate a combination of the invention and a method of using it to detect an mRNA target. The surface of the invention, shown in FIG. 2, contains 15 identical test regions; in an especially preferred embodiment of the invention, each of these test regions is a well in a microtiter plate. Each of the test regions contains six different anchors, here indicated as numbers 1–6. FIG. 1 schematically illustrates one of those anchors, anchor 1, which, in a most preferred embodiment of the invention, is an oligonucleotide. To anchor 1 is attached a linker molecule, linker 1, which comprises two portions. The first portion, which is specific for the anchor, is in this illustration an oligonucleotide which can hybridize specifically to the anchor. The second portion, which is a probe specific for the target of interest—here, target mRNA 1—is in this illustration an oligonucleotide which can hybridize to that target. Although not illustrated in this figure, each of the remaining five anchors can hybridize to its own linker via the anchor-specific portion; each linker can contain a probe portion specific for, e.g., an mRNA different from (or the same as) mRNA 1. This illustrated combination can be used to assay as many as 15 different samples at the same time for the presence of mRNA 1 (or, simultaneously, for mRNA targets which are specified (programmed) by the other five probes in the array). To perform the assay, each sample, which in this example can be an RNA extract from, say, one of 15 independent cell lines, is added in a small volume to one of the regions, or wells, and incubated under conditions effective for hybridization of the probe and the target. In order to determine if mRNA 1 is present in a sample, a detection device which can recognize patterns, and/or can interrogate specific locations within each region for the presence of a signal, is employed. If the cell lines are incubated under conditions in which their mRNAs are labeled in vivo with a tag, and if mRNA 1 is present in a sample, the detector will detect a signal emanating from the tagged mRNA at the location defined by anchor/probe complex 1. Alternatively, the mRNA can be directly labeled in vitro, before or after being added to the regions (wells). Alternatively, as is illustrated in FIG. 1, mRNA can be tagged indirectly, before or after it has hybridized to the probe, e.g., by incubating the RNA with a tagged "detector" oligonucleotide (target-specific reporter oligonucleotide) which is complementary to a sequence other than that recognized by the probe. In the illustrated example, 15 samples can be analyzed simultaneously. Because at least 20 or more, e.g. as many as 1536 or more, samples can be analyzed simultaneously with this invention, it is a very high throughput assay system.

As used herein, "target" refers to a substance whose presence, activity and/or amount is desired to be determined and which has an affinity for a given probe. Targets can be man-made or naturally-occurring substances. Also, they can be employed in their unaltered state or as aggregates with other species. Targets can be attached, covalently or noncovalently, to a binding member, either directly or via a specific binding substance. Examples of targets which can be employed in this invention include, but are not limited to, receptors (on vesicles, lipids, cell membranes or a variety of other receptors); ligands, agonists or antagonists which bind to specific receptors; polyclonal antibodies, monoclonal antibodies and antisera reactive with specific antigenic determinants (such as on viruses, cells or other materials); drugs; nucleic acids or polynucleotides (including mRNA, tRNA, rRNA, oligonucleotides, DNA, viral RNA or DNA, ESTs, cDNA, PCR-amplified products derived from RNA or DNA, and mutations, variants or modifications thereof); proteins (including enzymes, such as those responsible for cleaving neurotransmitters, proteases, kinases and the like); substrates for enzymes; peptides; cofactors; lectins; sugars; polysaccharides; cells; cellular membranes; organelles; etc., as well as other such molecules or other substances which can exist in complexed, covalently bonded crossliriked, etc. form. As used herein, the terms nucleic acid, polynucleotide, polynucleic acid and oligonucleotide are interchangeable. Targets can also be referred to as anti-probes.

As used herein, a "probe" is a substance, e.g., a molecule, that can be specifically recognized by a particular target. The types of potential probe/target or target/probe binding partners include receptor/ligand; ligand/antiligand; nucleic acid (polynucleotide) interactions, including DNA/DNA, DNA/RNA, PNA (peptide nucleic acid)/nucleic acid; enzymes, other catalysts, or other substances, with substrates, small molecules or effector molecules; etc. Examples of probes that are contemplated by this invention include, but are not limited to, organic and inorganic materials or polymers, including metals, chelating agents or other compounds which interact specifically with metals, plastics, agonists and antagonists for cell membrane receptors, toxins and venoms, viral epitopes, hormones (e.g., opioid peptides, steroids, etc.), hormone receptors, lipids (including phospholipids), peptides, enzymes (such as proteases or kinases), enzyme substrates, cofactors, drugs, lectins, sugars, nucleic acids (including oligonucleotides, DNA, RNA, PNA or modified or substituted nucleic acids), oigosaccharides, proteins, enzymes, polyclonal and monoclonal antibodies, single chain antibodies, or fragments thereof. Probe polymers can be linear or cyclic. Probes can distinguish between phosphorylated and non-phosphorylated proteins, either by virtue of differential activity or differential binding. Probes such as lectins can distinguish among glycosylated proteins. As used herein, the terms nucleic acid, polynucleotide, polynucleic acid and oligonucleotide are interchangeable. Any of the substances described above as "probes" can also serve as "targets," and vice-versa.

Any compatible surface can be used in conjunction with this invention. The surface (usually a solid) can be any of a variety of organic or inorganic materials or combinations thereof, including, merely by way of example, plastics such as polypropylene or polystyrene; ceramic; silicon; (fused) silica, quartz or glass, which can have the thickness of, for example, a glass microscope slide or a glass cover slip; paper, such as filter paper; diazotized cellulose; nitrocellulose filters; nylon membrane; or polyacrylamide gel pad. Substrates that are transparent to light are useful when the method of performing an assay involves optical detection. In a preferred embodiment, the surface is the plastic surface of a multiwell, e.g., tissue culture dish, for example a 24-, 96-, 256-, 384-, 864- or 1536-well plate (e.g., a modified plate such as a Corning Costar DNA Bind plate). Anchors can be associated, e.g., bound, directly with a surface, or can be associated with one type of surface, e.g., glass, which in turn is placed in contact with a second surface, e.g., within a plastic "well" in a microtiter dish. The shape of the surface is not critical. It can, for example, be a flat surface such as a square, rectangle, or circle; a curved surface; or a three dimensional surface such as a bead, particle, strand, precipitate, tube, sphere; etc.

The surface comprises regions which are spatially discrete and addressable or identifiable. Each region comprises a set of anchors. How the regions are separated, their physical characteristics, and their relative orientation to one another are not critical. In one embodiment, the regions can be separated from one another by any physical barrier which is resistant to the passage of liquids. For example, in a preferred embodiment, the regions can be wells of a multiwell (e.g., tissue culture) dish, for example a 24-, 96-, 256-, 384-, 864- or 1536-well plate. Alternatively, a surface such as a glass surface can be etched out to have, for example, 864 or 1536 discrete, shallow wells. Alternatively, a surface can comprise regions with no separations or wells, for example a flat surface, e.g., piece of plastic, glass or paper, and individual regions can further be defined by overlaying a structure (e.g.,. a piece of plastic or glass) which delineates the separate regions. Optionally, a surface can already comprise one or more arrays of anchors, or anchors associated with linkers, before the individual regions are delineated. In another embodiment, arrays of anchors within each region can be separated from one another by blank spaces on the surface in which there are no anchors, or by chemical boundaries, such as wax or silicones, to prevent spreading of droplets. In yet another embodiment, the regions can be defined as tubes or fluid control channels, e.g., designed for flow-through assays, as disclosed, for example, in Beattie et al (1995). *Clin. Chem.* 4, 700–706. Regions within or on, etc. a surface can also be defined by modification of the surface itself. For example, a plastic surface can comprise portions made of modified or derivatized plastic, which can serve, e.g., as sites for the addition of specific types of polymers (e.g., PEG can be attached to a polystyrene surface and then derivatized with carboxyl or amino groups, double bonds, aldehydes, and the like). Alternatively, a plastic surface can comprise molded structures such as protrusions or bumps, which can serve as platforms for the addition of anchors. The relative orientation of the test regions can take any of a variety of forms including, but not limited to, parallel or perpendicular arrays within a square or rectangular or other surface, radially extending arrays within a circular or other surface, or linear arrays, etc.

The spatially discrete regions of the invention are present in multiple copies. That is, there are at least two, preferably at least twenty, or at least about 24, 50, 96, 256, 384, 864, 1536, 2025, or more, etc., substantially identical, spatially discrete (separated) regions. Increasing numbers of repeated regions can allow for assays of increasingly higher throughput. Substantially identical regions, as used herein, refers to regions which contain identical or substantially identical arrays of anchors and/or anchor/linker complexes. Substantially identical, as used herein, means that an array or region is intended to serve essentially the same function as another array or region in the context of analyzing a target in accordance with this invention. Differences not essentially affecting function, i.e., detectability of targets, are along the line of small nucleotide imperfections (omissions/inserts/substitutions) or oligo imperfections (poor surface binding), etc., which do not within assay accuracy significantly affect target determination results.

Of course, one of skill in the art will recognize that not all of the regions on a surface need to be substantially identical to one another. For example, if two different sets of arrays are to be tested in parallel, it might be advantageous to include both sets of arrays on a single surface. For example, the two different sets of arrays can be arranged in alternating striped patterns, to facilitate comparison between them. In another embodiment, the practitioner may wish to include one or more regions which can be detected in a distinguishable manner from the other regions on the surface and can thereby be used as a "registration region(s)." For example, a registration region can comprise oligonucleotides or peptides which display a distinctive pattern of fluorescent molecules that can be recognized by a scanning detection device as a "starting point" for aligning the locations of the regions on a surface.

The size and physical spacing of the test regions are not limiting. Typical regions are of an area of about 1 to about 700 mm$^2$, preferably 1 to about 40 mm$^2$, and are spaced about 0.5 to about 5 mm apart, and are routinely selected depending on the areas involved. In a preferred embodiment, the regions are spaced approximately 5 mm apart. For example, each region could comprise a rectangular grid, with, for example, 8 rows and 6 columns, of roughly circular spots of anchors which are about 100 micrometers in diameter and 500 micrometers apart; such a region would cover about a 20 millimeter square area. Larger and smaller region areas and spacings are included.

The regions can also be further subdivided such that some or all anchors within a region are physically separated from neighboring anchors by means, e.g., of an indentation or dimple. For example, the number of subdivisions (subregions) in a region can range from about 10 to about 100 or more or less. In one embodiment, a region which is a well of a 1536-well dish can be further subdivided into smaller wells, e.g., about 4 to about 900, preferably about 16 to about 36 wells, thereby forming an array of wells-within-wells. See FIG. 4. Such a dimpled surface reduces the tolerance required for physically placing a single anchor (or group of anchors) into each designated space (locus), and the size of the areas containing anchors is more uniform, thereby facilitating the detection of targets which bind to the probe.

The term "anchor" as used herein refers to any entity or substance, e.g., molecule (or "group" of substantially identical such substances (see, e.g., FIG. 7)) which is associated with (e.g., immobilized on, or attached either covalently or non-covalently to) the surface, or which is a portion of such surface (e.g., derivatized portion of a plastic surface), and which can undergo specific interaction or association with a linker or other substance as described herein. As used herein, an "anchor/linker complex" exists when an anchor and a linker have combined through molecular association in a specific manner. The interaction with the linker can be either irreversible, such as via certain covalent bonds, or reversible, such as via nucleic acid hybridization. In a preferred embodiment, the anchor is a nucleic acid, which can be of any length (e.g., an oligonucleotide) or type (e.g., DNA, RNA, PNA, or a PCR product of an RNA or DNA molecule). The nucleic acid can be modified or substituted (e.g., comprising non naturally occurring nucleotides such as, e.g., inosine; joined via various known linkages such as sulfamate, sulfamide, phosphorothionate, methylphosphonate, carbamate, etc.; or a semisynthetic molecule such as a DNA-streptavidin conjugate, etc.). Single stranded nucleic acids are preferred. The anchor can also be a peptide or a protein. For example, it can be a polyclonal or monoclonal antibody molecule or fragment thereof, or single chain antibody or fragment thereof, which binds specifically to the portion of a linker that is an antigen or an anti-antibody molecule; in the obverse, the anchor can be a peptide, and the portion of the linker which binds to it can be an antibody or the like. In another embodiment, the anchor can be a lectin (such as concanavalin A or agglutinins from organisms such as Limulus, peanut, mung bean, Phaseolus, wheat germ, etc.) which is specific for a particular carbohydrate. In another embodiment, the anchor can be an organic molecule, such as a modified or derivatized plastic polymer which can serve, e.g., as the stage for specific solid phase chemical synthesis of an oligonucleotide. In this case, the derivatized plastic can be distributed as an array of discrete, derivatized, loci which are formed integrally into the plastic surface of a combination during the manufacturing process. In another embodiment, the anchor can take advantage of specific or preferential binding between metal ions, e.g., Ni, Zn, Ca, Mg, etc. and particular proteins or chelating agents. For example, the anchor can be polyhistidine, and the anchor-specific portion of the linker can be nickel, which is attached via a nickel chelating agent to a target-specific probe. Alternatively, the chelating agent can be the anchor and the polyhistidine the probe-related portion. Alternatively, the anchor can be an inorganic substance. For example, it can be a metal such as calcium or magnesium, and the anchor-specific portion of the linker can be a preferential chelating agent, such as EDTA or EGTA, respectively, which is attached to a target-specific probe. One of skill in the art will recognize that a wide range of other types of molecules can also serve as anchors, such as those general types also discussed in conjunction with probes and targets.

The number of anchors in a test region can be at least two, preferably between about 8 and about 900 (more or less being included), more preferably between about 8 and about 300, and most preferably between about 30 and about 100 (e.g., about 64). In some preferred embodiments, there are about 16, 36, 45 or 100 anchors/test region for a surface with 96 test regions (e.g., wells), or about 9, 16 or 25 anchors/test region for a surface with 384 test regions (e.g., wells). In a most preferred embodiment, each anchor in a test region has a different specificity from every other anchor in the array. However, two or more of the anchors can share the same specificity and all of the anchors can be identical. In one embodiment, in which a combination of the invention comprises a very large number of test regions (e.g., about 864, 1536, or more), so that a large number of test samples can be processed at one time, it might of interest to test those samples for only a limited number (e.g., about 2, 4, 6 or 9) of parameters. In other words, for combinations comprising a very large number of regions, it might be advantageous to have only about 2 to 9 anchors per region.

The physical spacing and relative orientation of the anchors in or on a test region are not limiting. Typically, the distance between the anchors is about 0.003 to about 5 mm or less, preferably between about 0.03 and about 1. Larger and smaller anchor spacings (and areas) are included. The anchors can be arranged in any orientation relative to one another and to the boundaries of the region. For example, they can be arranged in a two-dimensional orientation, such as a square, rectangular, hexagonal or other array, or a circular array with anchors emanating from the center in radial lines or concentric rings. The anchors can also be arranged in a one-dimensional, linear array. For example, oligonucleotides can be hybridized to specific positions along a DNA or RNA sequence to form a supramolecular array. Alternatively, the anchors can be laid down in a "bar-code"-like formation. (See FIG. 6). For example, anchors can be laid down as long lines parallel to one another. The spacing between or the width of each long line can be varied in a regular way to yield a simple, recognizable pattern much like a bar-code, e.g., the first and third lines can be twice as large as the rest, lines can be omitted, etc. An extra empty line can be placed after the last line to demarcate one test region, and the bar code pattern can be repeated in succeeding test regions.

The pattern of anchors does not need to be in strict registry with the positions of the separated assay wells (test regions) or separate assay droplets. The term "assay positions" will be used to refer to the positions of the assay surface where assay samples are applied. (These can be defined by the position of separate droplets of assay sample or by the position of walls or separators defining individual assay wells on a multi-well plate for example.) The anchor pattern itself (e.g., a "bar code"-like pattern of oligonucleotide anchors) is used to define where exactly each separate anchor is positioned by pattern recognition—just as each line of a barcode is recognized by its position relative to the remaining lines. Hence the first anchor need not be at one edge or one corner of each assay position. The first anchor will be found by pattern recognition, rather than position relative to the assay position. As long as the area used by each assay position (the area of the droplet or the area of the well for example) is large enough to be certain to contain at least one whole unit of the repeating pattern of anchors, then each assay point will test the sample for that assay position for all of the targets specified by the (bar-coded) pattern wherever the pattern lies within the area of the assay position.

The anchors do not need to be arranged in a strict or even fixed pattern within each test region. For example, each anchor can be attached to a particle, bead, or the like, which assumes a random position within a test region. The location of each anchor can be determined by the use, e.g., of a detectable tag. For example, the linker molecule specific for each type of anchor can be labeled with a different fluorescent, luminescent etc. tag, and the position of a particle comprising a particular linker/anchor pair can be identified by the nature of the signal emanating from the linker, e.g., the excitation or emission spectrum. One skilled in the art can prepare a set of linkers with a variety of such attached tags, each with a distinguishable spectrum. Alternatively, the anchors can be labeled directly. For example, each type of anchor can be labeled with a tag which fluoresces with a different spectrum from the tags on other types of anchors. Alternatively, the particles, beads or the like can be different from one another in size or shape. Any of the labeling and detection methods described herein can be employed. For example, fluorescence can be measured by a CCD-based imaging system, by a scanning fluorescence microscope or Fluorescence Activated Cell Sorter (FACS).

An anchor can interact or become associated specifically with one portion—the anchor-specific portion—of a linker molecule. By the terms "interact" or "associate", it is meant herein that two substances or compounds (e.g., anchor and anchor-specific portion of a linker, a probe and its target, or a target and a target-specific reporter) are bound (e.g., attached, bound, hybridized, joined, annealed, covalently linked, or otherwise associated) to one another sufficiently that the intended assay can be conducted. By the terms "specific" or "specifically", it is meant herein that two components (e.g., anchor and anchor-specific region of a linker, a probe and its target, or a target and a target-specific reporter) bind selectively to each other and, in the absence of any protection technique, not generally to other components unintended for binding to the subject components. The parameters required to achieve specific interactions can be determined routinely, e.g., using conventional methods in the art.

For nucleic acids, for example, one of skill in the art can determine experimentally the features (such as length, base composition, and degree of complementarity) that will enable a nucleic acid (e.g., an oligonucleotide anchor) to hybridize to another nucleic acid (e.g., the anchor-specific portion of a linker) under conditions of selected stringency, while minimizing non-specific hybridization to other substances or molecules (e.g., other oligonucleotide linkers). Typically, the DNA or other nucleic acid sequence of an anchor, a portion of a linker, or a detector oligonucleotide will have sufficient complementarity to its binding partner to enable it to hybridize under selected stringent hybridization conditions, and the $T_m$ will be about 10° to 20° C. above room temperature (e.g., about 37° C.). In general, an oligonucleotide anchor can range from about 8 to about 50 nucleotides in length, preferably about 15, 20, 25 or 30 nucleotides. As used herein, "high stringent hybridization conditions" means any conditions in which hybridization will occur when there is at least 95%, preferably about 97 to 100%, nucleotide complementarity (identity) between the nucleic acids. However, depending on the desired purpose, hybridization conditions can be selected which require less complementarity, e.g., about 90%, 85%, 75%, 50%, etc. Among the hybridization reaction parameters which can be varied are salt concentration, buffer, pH, temperature, time of incubation, amount and type of denaturant such as formamide, etc. (see, e.g., Sambrook et al. (1989). *Molecular Cloning: A Laboratory Manual* (2d ed.) Vols. 1–3, Cold Spring Harbor Press, New York; Hames et al. (1985). *Nucleic Acid Hybridization*, IL Press; Davis et al. (1986), *Basic Methods in Molecular Biology*, Elsevir Sciences Publishing, Inc., New York). For example, nucleic acid (e.g., linker oligonucleotides) can be added to a test region (e.g., a well of a multiwell plate—in a preferred embodiment, a 96 or 384 or greater well plate), in a volume ranging from about 0.1 to about 100 or more µl (in a preferred embodiment, about 1 to about 50 µl, most preferably about 40 µl), at a concentration ranging from about 0.01 to about 5 µM (in a preferred embodiment, about 0.1 µM), in a buffer such as, for example, 6×SSPE-T (0.9 M NaCl, 60 mM NaH$_2$PO$_4$, 6 mM EDTA and 0.05% Triton X-100), and hybridized to a binding partner (e.g., an oligonucleotide anchor on the surface) for between about 10 minutes and about at least 3 hours (in a preferred embodiment, at least about 15 minutes) at a temperature ranging from about 4° C. to about 37° C. (in a preferred embodiment, at about room temperature). Conditions can be chosen to allow high throughput. In one embodiment of the invention, the reaction conditions can approximate physiological conditions.

The design of other types of substances or molecules (e.g., polypeptides, lectins, etc.) which can, e.g., serve as anchors or as portions of linkers, and the reaction conditions required to achieve specific interactions with their binding partners, are routine and conventional in the art (e.g, as described in Niemeyer et al (1994). *Nucl. Acids Res.* 22, 5530–5539; Fodor et al (1996). U.S. Pat. No. 5,510,270; Pirrung et al (1992), U.S. Pat. No. 5,143,854). Among the incubation parameters are buffer, salt concentration, pH, temperature, time of incubation, presence of carrier and/or agents or conditions to reduce non-specific interactions, etc. For example, to a test region (e.g., a well of a multiwell plate—in a preferred embodiment, a 96 or 384 or greater well plate) which contains, as anchors, antibodies, can be added anti-antibodies (e.g., antigens or antibody-specific secondary antibodies) in a volume ranging from about 0.1 to about 100 or more µl (in a preferred embodiment, about 1 to about 50 µl, most preferably about 40 µl), at a concentration ranging from about 10 pM to about 10 nM (in a preferred embodiment, about 1 nM), in a buffer such as, for example, 6×SSPE-T, PBS or physiological saline, and incubated with the anchors on the surface for between about 10 minutes and at least about 3 hours (in a preferred embodiment, at least about 15 minutes), at a temperature ranging from about 4° C. to about 45° C. (in a preferred embodiment, about 4° C.). For peptide anchors, a length of about 5 to about 20 amino acids is preferred.

In some embodiments of the invention, each anchor in an array can interact with the anchor-specific portion of its corresponding linker to substantially the same degree as do the other anchors in the array, under selected reaction conditions. This can insure that the anchors specify a substantially uniform array of linkers and, therefore, probes.

The anchors within a test region can be a "generic" set, each anchor of which can interact with one or more of a variety of different linkers, each having a portion specific to such anchor but with differing "probe" portions; thus, a single array of generic anchors can be used to program or define a varied set of probes. The flexible nature of such a generic assay of anchors can be illustrated with reference to FIGS. 1 and 2. FIG. 2 illustrates a surface which comprises 15 test regions, each of which contains an array of 6 different anchors, which in this example can be oligonucleotides. FIG. 1 schematically illustrates one of these (oligonucleotide) anchors, anchor 1, which is in contact with linker 1, which comprises one portion that is specific for anchor 1 and a second portion that is specific for target mRNA 1. Alternatively, one could substitute, e.g., a linker 2, which, like linker 1, comprises a portion that is specific for anchor 1, but which comprises a second portion that is specific for target mRNA 2 instead of target mRNA 1. Thus, anchor 1 can be used to specify (or program, or define, or determine) probes for either of two or more different target mRNAs. The process of generating and attaching a high resolution pattern (array) of oligonucleotides or peptides can be expensive, time-consuming and/or physically difficult. The ability to use a pre-formed array of anchors to program a wide variety of probe arrays is one advantage of this invention.

Although the generic anchors illustrated in FIG. 2 define a pattern of oligonucleotide probes, the identical anchor array could also be used to program an array of other probes, for example receptor proteins (see, e.g., FIG. 3). Clearly, many permutations are possible, given the range of types of anchor/linker interactions, e.g., even more complex layers of "sandwiched" or "piggybacked" probes such as protein/antibody combinations. Thus, the surface of anchors per this invention, itself, offers novel advantages.

In one embodiment of the invention, anchors can interact reversibly with linkers; thus, a generic set of anchors can be re-used to program a varied set of probes. For example, an oligonucleotide anchor can be separated from the oligonucleotide portion of a linker by, for example, a heating step that causes the two oligonucleotides to dissociate, and can then be rebound to a second linker. The ability to re-use anchor arrays, which can be expensive, time-consuming and/or physically difficult to make, is another advantage of the invention.

An anchor does not necessarily have to interact with a linker. For example, an anchor can be coupled (directly or indirectly) to a detectable molecule, such as a fluorochrome, and can thereby serve to localize a spot within a grid, e.g., for purpose of registration between the test surface and the detector. Alternatively, an anchor can be labeled with a known amount of a detectable molecule so as to serve as internal quantitation marker, e.g., for purposes of calibration.

The term "linker" as used herein refers to a bifunctional substance which comprises a first portion (or moiety or part) that is specific for a chosen (designated) anchor or subset of the anchors ("anchor-specific") and a second portion that is a probe which is specific for a target of interest ("target-specific"). The two portions of the linker can be attached via covalent or noncovalent linkages, and can be attached directly or through an intermediate.

The chemical nature of the anchor-specific portion of the linker is, of course, a function of the anchor or anchors with which it interacts. For example, if the anchor is an oligonucleotide, the portion of the linker which interacts with it can be, for example, a peptide which binds specifically to the oligonucleotide, or a nucleic acid which can hybridize efficiently and specifically to it under selected stringent hybridization conditions. The nucleic acid can be, e.g., an oligonucleotide, DNA, RNA, PNA, PCR product, or substituted or modified nucleic acid (e.g., comprising non naturally-occurring nucleotides such as, e.g., inosine; joined via various known linkages such as sulfamate, sulfamide, phosphorothionate, methylphosphonate, carbamate; or a semisynthetic molecule such as a DNA-streptavidin conjugate, etc.). Single strand moieties are preferred. The portion of a linker which is specific for an oligonucleotide anchor can range from about 8 to about 50 nucleotides in length, preferably about 15, 20, 25 or 30 nucleotides. If the anchor is an antibody, the portion of the linker which interacts with it can be, e.g., an anti-antibody, an antigen, or a smaller fragment of one of those molecules, which can interact specifically with the anchor. Substances or molecules which interact specifically with the other types of anchors described above, and which can serve as the anchor-specific portion of a linker, are well-known in the art and can be designed using conventional procedures (e.g., see above).

The chemical nature of the target-specific portion of the linker is, of course, a function of the target for which it is a probe and with which it interacts. For example, if the target is a particular mRNA, the target-specific portion of the linker can be, e.g., an oligonucleotide which binds specifically to the target but not to interfering RNAs or DNAs, under selected hybridization conditions. One of skill in the art can, using art-recognized methods, determine experimentally the features of an oligonucleotide that will hybridize optimally to the target, with minimal hybridization to non-specific, interfering DNA or RNA (e.g., see above). In general, the length of an oligonucleotide probe used to distinguish a target mRNA present in a background of a large excess of untargeted RNAs can range from about 8 to about 50 nucleotides in length, preferably about 18, 20, 22 or 25 nucleotides. An oligonucleotide probe for use in a biochemical assay in which there is not a large background of competing targets can be shorter. Using art-recognized procedures (e.g., the computer program BLAST), the sequences of oligonucleotide probes can be selected such that they are mutually unrelated and are dissimilar from potentially interfering sequences in known genetics databases. The selection of hybridization conditions that will allow specific hybridization of an oligonucleotide probe to an RNA can be determined routinely, using art-recognized procedures (e.g., see above). For example, target RNA [e.g., total RNA or mRNA extracted from tissues or cells grown (and optionally treated with an agent of interest) in any vessel, such as the well of a multiwell microtiter plate (e.g., 96 or 384 or more wells)] can be added to a test region containing a oligonucleotide probe array (see above) in a buffer such as 6×SSPE-T or others, optionally containing an agent to reduce non-specific binding (e.g., about 0.5 mg/ml degraded herring or salmon sperm DNA, or yeast RNA), and incubated at an empirically determined temperature for a period ranging from between about 10 minutes and at least 18 hours (in a preferred embodiment, about 3 hours). The stringency of the hybridization can be the same as, or less than, the stringency employed to associate the anchors with the anchor-specific portion of the linkers. The design and use of other types of probes are also routine in the art, e.g., as discussed above.

The anchor-specific and the target-specific portions of a linker can be joined (attached, linked) by any of a variety of covalent or non-covalent linkages, the nature of which is not essential to the invention. The two portions can be joined directly or through an intermediate molecule. In one embodiment, in which both portions of the linker are oligonucleotides, they can be joined by covalent linkages such as phosphodiester bonds to form a single, colinear nucleic acid. In another embodiment, in which the anchor-specific portion is an oligonucleotide and the target-specific portion is a receptor, for example a receptor protein, the two portions can be joined via the interaction of biotin and streptavidin molecules, an example of which is illustrated in FIG. 3. Many variations of such linkages are known (e.g., see Niemeyer et al (1994). *NAR* 22, 5530–5539). Alternatively, the two portions can be joined directly, e.g., an oligonucleotide can be amidated and then linked directly (e.g., crosslinked) to a peptide or protein via an amide bond, or joined to a membrane component via an amide bond or a lipid attachment. Methods to form such covalent or noncovalent bonds are conventional and are readily optimized by one of skill in the art.

After two substances are associated (e.g., by incubation of two nucleic acids, two proteins, a protein plus a nucleic acid, or others) to form a complex (such as, e.g., an anchor/linker complex), the resulting complex can be optionally treated (e.g., washed) to remove unbound substances (e.g., linkers), using conditions which are determined empirically to leave specific interactions intact, but to remove non-specifically bound material. For example, reaction mixtures can be washed between about one and ten times or more under the same or somewhat more stringent conditions than those used to achieve the complex (e.g., anchor/linker complex).

The combinations of this invention can be manufactured routinely, using conventional technology.

Some of the surfaces which can be used in the invention are readily available from commercial suppliers. In a preferred embodiment, the surface is a 96-, 384- or 1536-well microtiter plate such as modified plates sold by Corning Costar. Alternatively, a surface comprising wells which, in turn, comprise indentations or "dimples" can be formed by micromachining a substance such as aluminum or steel to prepare a mold, then microinjecting plastic or a similar material into the mold to form a structure such as that illustrated in FIG. 4. Alternatively, a structure such as that shown in FIG. 4, comprised of glass, plastic, ceramic, or the like, can be assembled, e.g., from three pieces such as those illustrated in FIG. 5: a first section, called a well separator (FIG. 5a), which will form the separations between the sample wells; a second section, called a subdivider (FIG. 5b), which will form the subdivisions, or dimples, within each test well; and a third section, called a base (FIG. 5c), which will form the base of the plate and the lower surface of the test wells. The separator can be, for example, a piece of material, e.g., silicone, with holes spaced throughout, so that each hole will form the walls of a test well when the three pieces are joined. The subdivider can be, for example, a thin piece of material, e.g., silicone, shaped in the form of a screen or fine meshwork. The base can be a flat piece of material, e.g., glass, in, for example, the shape of the lower portion of a typical microplate used for a biochemical assay. The top surface of the base can be flat, as illustrated in FIG. 5c, or can be formed with indentations that will align with the subdivider shape to provide full subdivisions, or wells, within each sample well. The three pieces can be joined by standard procedures, for example the procedures used in the assembly of silicon wafers.

Oligonucleotide anchors, linker moieties, or detectors can be synthesized by conventional technology, e.g., with a commercial oligonucleotide synthesizer and/or by ligating together subfragments that have been so synthesized. In one embodiment of the invention, preformed nucleic acid anchors, such as oligonucleotide anchors, can be situated on or within the surface of a test region by any of a variety of conventional techniques, including photolithographic or silkscreen chemical attachment, disposition by ink jet technology, capillary, screen or fluid channel chip, electrochemical patterning using electrode arrays, contacting with a pin or quill, or denaturation followed by baking or UV-irradiating onto filters (see, e.g., Rava et al (1996). U.S. Pat. No. 5,545,531; Fodor et al (1996). U.S. Pat. No. 5,510,270; Zanzucchi et al (1997). U.S. Pat. No. 5,643,738; Brennan (1995). U.S. Pat. No. 5,474,796; PCT WO 92/10092; PCT WO 90/15070). Anchors can be placed on top of the surface of a test region or can be, for example in the case of a polyacrylamide gel pad, imbedded within the surface in such a manner that some of the anchor protrudes from the surface and is available for interactions with the linker. In a preferred embodiment, preformed oligonucleotide anchors are derivatized at the 5' end with a free amino group; dissolved at a concentration routinely determined empirically (e.g., about 1 µM) in a buffer such as 50 mM phosphate buffer, pH 8.5 and 1 mM EDTA; and distributed with a Pixus nanojet dispenser (Cartesian Technologies) in droplets of about 10.4 nanoliters onto specific locations within a test well whose upper surface is that of a fresh, dry DNA Bind plate (Corning Costar). Depending on the relative rate of oligonucleotide attachment and evaporation, it may be required to control the humidity in the wells during preparation. In another embodiment, oligonucleotide anchors can be synthesized directly on the surface of a test region, using conventional methods such as, e.g., light-activated deprotection of growing oligonucleotide chains (e.g., in conjunction with the use of a site directing "mask") or by patterned dispensing of nanoliter droplets of deactivating compound using a nanojet dispenser. Deprotection of all growing sequences that are to receive a single nucleotide can be done, for example, and the nucleotide then added across the surface.

Peptides, proteins, lectins, chelation embodiments, plastics and other types of anchors or linker moieties can also be routinely generated, and anchors can be situated on or within surfaces, using appropriate available technology (see, e.g., Fodor et al (1996). U.S. Pat. No. 5,510,270; Pirrung et al (1992). U.S. Pat. No. 5,143,854; Zanzucchi et al (1997). U.S. Pat. No. 5,643,738; Lowe et al (1985). U.S. Pat. No. 4,562,157; Niemeyer et al (1994). NAR 22, 5530–5539).

In some embodiments of the invention, the disclosed combinations are used in a variety of screening procedures and/or to obtain information about the level, activity or structure of the probes or target molecules. Such assays are termed Multi Array Plate Screen (MAPS) methods or assays, and the surfaces comprising arrays of anchors or anchors plus probes which are used for the assays are termed MAPS arrays or MAPS plates.

The components of a reaction mixture, assay, or screening procedure can be assembled in any order. For example, the anchors, linkers and targets can be assembled sequentially; or targets and linkers, in the presence or absence of reporters, can be assembled in solution and then contacted with the anchors.

One embodiment of the invention relates to a method of detecting at least one target, comprising a) contacting a sample which may comprise said target(s) with a bifunctional linker which has a first portion that is specific for an oligonucleotide anchor and a second portion that comprises a probe which is specific for said target(s), under conditions effective to obtain a first hybridization product between said target(s) and said linker, b) contacting said first hybridization product with a combination under conditions effective to obtain a second hybridization product between said first hybridization product and said combination, wherein said combination comprises, before the addition of said first hybridization product, 1) a surface comprising multiple spatially discrete regions, at least two of which are substantially identical, each region comprising 2) at least 8 different oligonucleotide anchors, c) contacting said first hybridization product or said second hybridization product with a labeled detector probe, and d) detecting said detection probe.

Each of the assays or procedures described below can be performed in a high throughput manner, in which a large number of samples (e.g., as many as about 864, 1036, 1536, 2025 or more, depending on the number of regions in the combination) are assayed on each plate or surface rapidly and concurrently. Further, many plates or surfaces can be processed at one time. For example, in methods of drug discovery, a large number of samples, each comprising a drug candidate (e.g., a member of a combinatorial chemistry library, such as variants of small molecules, peptides, oligonucleotides, or other substances), can be added to separate regions of a combination as described or can be added to biological or biochemical samples that are then added to separate regions of a combination, and incubated with probe arrays located in the regions; and assays can be performed on each of the samples. With the recent advent and continuing development of high-density microplates, DNA spotting tools and of methods such as laser technology to generate and collect data from even denser microplates, robotics, improved dispensers, sophisticated detection systems and data-management software, the methods of this invention can be used to screen or analyze thousands or tens of thousands or more of compounds per day.

For example, in embodiments in which the probes are oligonucleotides, the assay can be a diagnostic nucleic acid or polynucleotide screen (e.g., a binding or other assay) of a large number of samples for the presence of genetic variations or defects (e.g., polymorphisms or specific mutations associated with diseases such as cystic fibrosis. See, e.g., Iitia et al (1992). *Molecular and Cellular Probes* 6, 505–512)); pathogenic organisms (such as bacteria, viruses, and protozoa, whose hosts are animals, including humans, or plants), or mRNA transcription patterns which are diagnostic of particular physiological states or diseases. Nucleic acid probe arrays comprising portions of ESTs (including full-length copies) can be used to evaluate transcription patterns produced by cells from which the ESTs were derived (or others). Nucleic acid probes can also detect peptides, proteins, or protein domains which bind specifically to particular nucleic acid sequences (and vice-versa).

In another embodiment, the combinations of the invention can be used to monitor biochemical reactions such as, e.g., interactions of proteins, nucleic acids, small molecules, or the like—for example the efficiency or specificity of interactions between antigens and antibodies; or of receptors (such as purified receptors or receptors bound to cell membranes) and their ligands, agonists or antagonists; or of enzymes (such as proteases or kinases) and their substrates, or increases or decreases in the amount of substrate converted to a product; as well as many others. Such biochemical assays can be used to characterize properties of the probe or target, or as the basis of a screening assay. For example, to screen samples for the presence of particular proteases (e.g., proteases involved in blood clotting such as proteases Xa and VIIa), the samples can be assayed on combinations in which the probes are fluorogenic substrates specific for each protease of interest. If a target protease binds to and cleaves a substrate, the substrate will fluoresce, usually as a result, e.g., of cleavage and separation between two energy transfer pairs, and the signal can be detected. In another example, to screen samples for the presence of a particular kinase(s) (e.g., Src, tyrosine kinase, or ZAP70), samples containing one or more kinases of interest can be assayed on combinations in which the probes are peptides which can be selectively phosphorylated by one of the kinases of interest. Using art-recognized, routinely determinable conditions, samples can be incubated with the array of substrates, in an appropriate buffer and with the necessary cofactors, for an empirically determined period of time. (In some assays, e.g., for biochemical studies of factors that regulate the activity of kinases of interest, the concentration of each kinase can be adjusted so that each substrate is phosphorylated at a similar rate.) After treating (e.g., washing) each reaction under empirically determined conditions to remove kinases and undesired reaction components (optionally), the phosphorylated substrates can be detected by, for example, incubating them with detectable reagents such as, e.g., fluorescein-labeled anti-phosphotyrosine or anti-phosphoserine antibodies (e.g., at a concentration of about 10 nM, or more or less), and the signal can be detected. In another example, binding assays can be performed. For example, SH2 domains such as GRB2 SH2 or ZAP70 SH2 can be assayed on probe arrays of appropriate phosphorylated peptides; or blood sera can be screened on probe arrays of particular receptors for the presence of immune deficiencies. Also, enzyme-linked assays can be performed in such an array format. Combinations of the invention can also be used to detect mutant enzymes, which are either more or less active than their wild type counterparts, or to screen for a variety of agents including herbicides or pesticides.

Of course, MAPS assays can be used to quantitate (measure, quantify) the amount of active target in a sample, provided that probe is not fully occupied, that is, not more than about 90% of available probe sites are bound (or reacted or hybridized) with target. Under these conditions, target can be quantitated because having more target will result in having more probe bound. On the other hand, under conditions where more than about 90% of available probe sites are bound, having more target present would not substantially increase the amount of target bound to probe. Any of the heretofore-mentioned types of targets can be quantitated in this manner. For example, Example 6 describes the quantitation of oligonucleotide targets. Furthermore, it demonstrates that even if a target is present in large excess (e.g., if it is present in such large amounts that it saturates the amount of available probe in a MAPS probe array), by adding known amounts of unlabeled target to the binding mixture, one can "shift the sensitivity" of the reaction in order to allow even such large amounts of target to be quantitated.

In another embodiment, combinations of the invention can be used to screen for agents which modulate the interaction of a target and a given probe. An agent can modulate the target/probe interaction by interacting directly or indirectly with either the probe, the target, or a complex formed by the target plus the probe. The modulation can take a variety of forms, including, but not limited to, an increase or decrease in the binding affinity of the target for the probe, an increase or decrease in the rate at which the target and the probe bind, a competitive or non-competitive inhibition of the binding of the probe to the target, or an increase or decrease in the activity of the probe or the target which can, in some cases, lead to an increase or decrease in the probe/target interaction. Such agents can be man-made or naturally-occurring substances. Also, such agents can be employed in their unaltered state or as aggregates with other species; and they can be attached, covalently or noncovalently, to a binding member, either directly or via a specific binding substance. For example, to identify potential "blood thinners," or agents which interact with one of the cascade of proteases which cause blood clotting, cocktails of the proteases of interest can be tested with a plurality of candidate agents and then tested for activity as described above. Other examples of agents which can be employed by this invention are very diverse, and include pesticides and herbicides. Examples 16 and 17 describe high throughput assays for agents which selectively inhibit specific kinases, or for selective inhibitors of the interaction between SH2 domains and phosphorylated peptides.

In another embodiment, the combinations of the invention can be used to screen for agents which modulate a pattern of gene expression. Arrays of oligonucleotides can be used, for example, to identify mRNA species whose pattern of expression from a set of genes is correlated with a particular physiological state or developmental stage, or with a disease condition ("correlative" genes, RNAs, or expression patterns). By the terms "correlate" or "correlative," it is meant that the synthesis pattern of RNA is associated with the physiological condition of a cell, but not necessarily that the expression of a given RNA is responsible for or is causative of a particular physiological state. For example, a small subset of mRNAs can be identified which are expressed, up-regulated and/or down-regulated in cells which serve as a model for a particular disease state; this altered pattern of expression as compared to that in a normal cell, which does not exhibit a pathological phenotype, can serve as a indicator of the disease state ("indicator" genes, RNAs, or expression patterns). The terms "correlative" and "indicator" can be used interchangeably. For example, cells treated with a tumor promoter such as phorbol myristate might exhibit a pattern of gene expression which mimics that seen in the early stages of tumor growth. In another model for cancer, mouse insulinoma cells (e.g., cell line TGP61), when infected with adenovirus, exhibit an increase in the expression of, e.g., c-Jun and MIP-2, while the expression of housekeeping genes such as GAPDH and L32 remains substantially unaffected.

Agents which, after contacting a cell from a disease model, either directly or indirectly, and either in vivo or in vitro (e.g., in tissue culture), modulate the indicator expression pattern, might act as therapeutic agents or drugs for organisms (e.g., human or other animal patients, or plants) suffering from the disease. Agents can also modulate expression patterns by contacting the nucleic acid directly, e.g., in an in vitro (test tube) expression system. As used herein, "modulate" means to cause to increase or decrease the amount and/or activity of a molecule or the like which is involved in a measurable reaction. The combinations of the invention can be used to screen for such agents. For example, a series of cells (e.g., from a disease model) can be contacted with a series of agents (e.g., for a period of time ranging from about 10 minutes to about 48 hours or more) and, using routine, art-recognized methods (e.g., commercially available kits), total RNA or mRNA extracts can be made. If it is desired to amplify the amount of RNA, standard procedures such as RT-PCR amplification can be used (see, e.g., Innis et al eds., (1996) *PCR Protocols: A Guide to Methods in Amplification,* Academic Press, New York). The extracts (or amplified products from them) can be allowed to contact (e.g., incubate with) a plurality of substantially identical arrays which comprise probes for appropriate indicator RNAs, and those agents which are associated with a change in the indicator expression pattern can be identified. Example 15 describes a high throughput assay to screen for compounds which may alter the expression of genes that are correlative with a disease state.

Similarly, agents can be identified which modulate expression patterns associated with particular physiological states or developmental stages. Such agents can be manmade or naturally-occurring substances, including environmental factors such as substances involved in embryonic development or in regulating physiological reactions, or substances important in agribusiness such as pesticides or herbicides. Also, such agents can be employed in their unaltered state or as aggregates with other species; and they can be attached, covalently or noncovalently, to a binding member, either directly or via a specific binding substance.

Another embodiment of the invention is a kit useful for the detection of at least one target in a sample, which comprises:

a) a surface, comprising multiple spatially discrete regions, at least two of which are substantially identical, each region comprising at least eight different anchors (oligonucleotide, or one of the other types described herein), and b) a container comprising at least one bifunctional linker molecule, which has a first portion specific for at least one of said anchor(s) and a second portion that comprises a probe which is specific for at least one of said target(s).

In one embodiment, there is provided a surface as in a) above and a set of instructions for attaching to at least one of said anchors a bifunctional linker molecule, which has a first portion specific for at least one of said anchor(s) and a second portion that comprises a probe which is specific for at least one target. The instructions can include, for example (but are not limited to), a description of each of the anchors on the surface, an indication of how many anchors there are and where on the surface they are located, and a protocol for specifically attaching (associating, binding, etc.) the linkers to the anchors. For example, if the anchors are oligonucleotides, the instructions can include the sequence of each anchor, from which a practitioner can design complementary anchor-specific moieties of linkers to interact specifically with (e.g., hybridize to) the anchors; if the anchors are peptides, the instructions can convey information about, e.g., antibodies which will interact specifically with the peptides. The instructions can also include a protocol for associating the anchors and linkers, e.g., conditions and reagents for hybridization (or other type of association) such as temperature and time of incubation, conditions and reagents for removing unassociated molecules (e.g., washes), and the like. Furthermore, the instructions can include information on the construction and use of any of the types of control linkers discussed herein, and of methods, e.g., to quantitate, normalize, "fine-tune" or calibrate assays to be performed with the combinations. The instructions can encompass any of the parameters, conditions or embodiments disclosed in this application, all of which can be performed routinely, with conventional procedures, by one of skill in the art.

As discussed elsewhere in this application, a practitioner can attach to a surface of the invention comprising a given array (or arrays) of anchors, a wide variety of types of linkers, thereby programming any of a wide variety of probe arrays. Moreover, a practitioner can remove a given set of linkers from a surface of the invention and add to it another set of linkers (either the same or different from the first set), allowing a given surface to be reused many times. This flexibility and reusability constitute further advantages of the invention.

In another embodiment, combinations of the invention can be used to map ESTs (Expressed Sequence Tags). That is, MAPS assays can be used to determine which, if any, of a group of ESTs were generated from different (or partially overlapping) portions of the same gene(s), and which, if any, are unique. FIGS. 18, 19, 20 and 21 illustrate such an assay, in this example an assay to determine which, if any, of 16 ESTs are "linked" to a common gene. A first step of the assay (see FIG. 18) is to assemble arrays in which each of the ESTs to be mapped is represented by at least one oligonucleotide probe that corresponds to it. A number of arrays equal to (or greater than) the number of ESTs to be mapped are distributed in separate regions (e.g., wells) of a surface; in the illustrated example, the surface of the combination comprises 16 wells, each of which contains an array of 16 different EST-specific oligonucleotides, numbered 1–16. An oligonucleotide which "corresponds to" an EST (is "EST-specific") is one that is sufficiently complementary to an EST such that, under selected stringent hybridization conditions, the oligonucleotide will hybridize specifically to that EST, but not to other, unrelated ESTs. An EST-corresponding oligonucleotide of this type can bind specifically (under optimal conditions) to the coding or non-coding strand of a cDNA synthesized from the gene from which the EST was originally generated or to an mRNA synthesized from the gene from which the EST was originally generated. Factors to be considered in designing oligonucleotides, and hybridization parameters to be optimized in order to achieve specific hybridization, are discussed elsewhere in this application. In order to assemble the arrays, linker molecules are prepared, each of which comprises a moiety specific for one of the anchors of a generic array plus a moiety comprising an oligonucleotide probe that corresponds to one of the ESTs to be mapped; and the linkers are attached to anchors as described elsewhere in this application. In a subsequent step, an aliquot of a sample comprising a mixture of nucleic acids (e.g., mRNA or single stranded or denatured cDNA), which may contain sequences that are complementary to one or more of the oligonucleotide probes, is added to each of the regions (wells) which comprises a probe array; the mixture is then incubated under routinely determined optimal conditions, thereby permitting nucleic acid to bind to complementary probes. If several of the EST-specific probes are complementary to different portions of a single nucleic acid, that nucleic acid will bind to each of the loci in the array at which one of those probes is located.

In a subsequent step, a different detector oligonucleotide (in the illustrated example, detectors #1 to 16) is added to each region (well) (see FIG. 19). A detector oligonucleotide is designed for each of the ESTs to be mapped. Each EST-specific detector corresponds to a different (at least partially non-overlapping) portion of the EST than does the probe oligonucleotide, so that the probe and the detector oligonucleotides do not interfere with one another. Consider, for example, the ESTs depicted in FIG. 21, which correspond to ESTs 1, 2 and 6 of FIGS. 18–20. FIG. 21 indicates that ESTs #1 and #2 were both obtained from gene X (they are "linked"), whereas EST #6 was obtained from a different, unrelated gene. If aliquots of a sample containing a mixture of mRNAs, including one generated from gene X, are incubated with the probe arrays shown in FIGS. 18–20, the gene X mRNA will, under optimal conditions, hybridize at the loci with probes 1 and 2, but not at those with probe 6. (Of course, each mRNA must be added in molar excess over the sum of the probes to which it can hybridize.) If detector oligonucleotide 1 is added to region (well) 1, it will hybridize to the gene X mRNA which is bound at loci 1 and 2 of the probe array, but not at locus 6. Similarly, if detector oligonucleotide 2 is added to another well—say, well #2—it will also bind at loci 1 and 2, but not 6. In this fashion, one can determine in a high throughput manner which of the ESTs are linked, i.e. code for portions of the same gene, and which ESTs are unique. For the hypothetical example shown in FIG. 20, the first 3 ESTs encode portions of the same gene, the last 5 ESTs encode portions of another gene, and the remaining ESTs appear not to be linked. Conditions of hybridization, optional wash steps, methods of detection, and the like are discussed elsewhere in this application with regard to other MAPS assays. In order to confirm the linkage data obtained by the MAPS assay, one could perform PCR reactions using pairs of EST-specific oligonucleotide probes as sense and anti-sense primers. Every pair of linked ESTs should yield a PCR product. Note that this pairwise PCR test could be performed to determine linkage directly without using the Linkage MAPS assay; however, many reactions would be required, and each EST primer would have to be synthesized as both sense and anti-sense strands. For the illustrated example, 180 such reactions would be required.

In one aspect, the invention relates to a method of determining which of a plurality of ESTs are complementary to a given nucleic acid, comprising, a) incubating an immobilized array of oligonucleotide probes, at least one of which corresponds to each of said ESTs, with a test sample which may contain said given nucleic acid, to obtain a hybridization product between said oligonucleotide probes and said nucleic acid, b) incubating said hybridization product with a detector oligonucleotide, which corresponds to an EST to which one of said oligonucleotide probes corresponds, but which is specific for a different portion of the EST than is said oligonucleotide probe, and c) detecting which oligonucleotide probes of said array are labeled by said detector oligonucleotide, wherein said array of oligonucleotide probes is immobilized on a region of a combination, wherein said combination comprises 1) a surface comprising a number of spatially discrete, substantially identical, regions equal to the number of ESTs to be studied, each region comprising 2) a number of different anchors equal to the number of ESTs to be studied, each anchor in association with 3) a bifunctional linker which has a first portion that is specific for the anchor, and a second portion that comprises an oligonucleotide probe which corresponds to at least one of said ESTs.

In another aspect, the invention relates to a method as above, wherein one or more of said ESTs may be complementary to said nucleic acid, and wherein each of said ESTs comprises two different oligonucleotide sequences, the first of which defines an oligonucleotide probe corresponding to said EST, and the second of which defines a detector oligonucleotide corresponding to said EST, comprising, a) contacting a sample which comprises molecules of said nucleic acid with at least one region of a combination, wherein said region comprises an array of oligonucleotide probes, at least one of which corresponds to each of said ESTs, b) incubating said sample with said region, thereby permitting molecules of said nucleic acid to bind to said EST-corresponding oligonucleotide probes which are complementary to portions of said nucleic acid, c) incubating said region comprising molecules of said nucleic acid bound to one or more of said EST-corresponding oligonucleotide probes with a detector oligonucleotide which corresponds to an EST to which a given one of the oligonucleotide probes of said array corresponds, thereby binding detector oligonucleotides to nucleic acid molecules which have bound to said given oligonucleotide probe or to other oligonucleotide probes which are complementary to said nucleic acid, d) detecting the presence of said detector oligonucleotides, thereby identifying which EST-corresponding oligonucleotide probes of said array are complementary to portions of a nucleic acid which binds to said given oligonucleotide EST-corresponding probe, thereby identifying which ESTs are complementary to said given nucleic acid wherein said array of oligonucleotide probes is immobilized on a region of a combination, wherein said combination comprises 1) a surface comprising a number of spatially discrete, substantially identical regions equal to the number of ESTs to be studied, each region comprising 2) a number of different anchors equal to the number of ESTs to be studied, each anchor in association with 3) a bifunctional linker which has a first portion that is specific for the anchor, and a second portion that comprises an oligonucleotide probe which corresponds to at least one of said ESTs.

The components of an EST mapping assay can be assembled in any order. For example, the anchors, linkers and ESTs can be assembled sequentially; or linkers and ESTs, in the presence or absence of reporters, can be assembled in solution and then added to the anchors.

In another aspect, the invention relates to a method of determining which of a plurality of ESTs are complementary to a given nucleic acid, comprising, a) incubating a collection of bifunctional oligonucleotide linker molecules, each of which comprises a first portion which is a probe that corresponds to at least one of said ESTs, and a second portion which is specific for an anchor oligonucleotide, with a test sample which may contain said given nucleic acid, to obtain a first hybridization product between said oligonucleotide probes and said nucleic acid, b) incubating said first hybridization product with an immobilized array of anchor oligonucleotides, wherein each anchor oligonucleotide corresponds to the anchor-specific portion of at least one of said linker molecules, to form a second hybridization product comprising said anchors, said oligonucleotide probes and said nucleic acid, and c) incubating either said first or said second hybridization product with a detector oligonucleotide, which corresponds to an EST to which one of said oligonucleotide probes corresponds, but which is specific for a different portion of the EST than is said oligonucleotide probe, and d) detecting which oligonucleotide probes of said array are labeled by said detector oligonucleotide, wherein said array of anchor oligonucleotides is immobilized on a region of a combination, wherein said combination comprises
1) a surface comprising a number of spatially discrete, substantially identical, regions equal to the number of ESTs to be studied, each region comprising
2) a number of different anchors equal to the number of ESTs to be studied.

Of course, the above methods for mapping ESTs can be used to map test sequences (e.g., polynucleotides) onto any nucleic acid of interest. For example, one can determine if two or more cloned DNA fragments or cDNAs map to the same genomic DNA. Such a procedure could aid, for example, in the structural elucidation of long, complex genes. In a similar manner, one can determine if one or more spliced out sequences or coding sequences map to the same genomic DNA. Such a determination could be used, for example, in a diagnostic test to distinguish between a normal and a disease condition which are characterized by differential splicing patterns. Many other applications of the mapping method will be evident to one of skill in the art.

In another aspect, the invention relates to a method of determining which of a plurality of polynucleotides are complementary to a given nucleic acid, wherein one or more of said polynucleotides may be complementary to said nucleic acid, and wherein each of said polynucleotides comprises two different oligonucleotide sequences, the first of which defines an oligonucleotide probe corresponding to said polynucleotide, and the second of which defines a detector oligonucleotide corresponding to said polynucleotide, comprising, a) contacting a sample which comprises molecules of said nucleic acid with at least one region of a combination, wherein said region comprises an array of oligonucleotide probes, at least one of which corresponds to each of said polynucleotides, b) incubating said sample with said region, thereby permitting molecules of said nucleic acid to bind to said polynucleotide-corresponding oligonucleotide probes which are complementary to portions of said nucleic acid, c) incubating said region comprising molecules of said nucleic acid bound to one or more of said polynucleotide-corresponding oligonucleotide probes with a detector oligonucleotide which corresponds to a polynucleotide to which a given one of the oligonucleotide probes of said array corresponds, thereby binding detector oligonucleotides to nucleic acid molecules which have bound to said given oligonucleotide probe or to other oligonucleotide probes which are complementary to said nucleic acid, d) detecting the presence of said detector oligonucleotides, thereby identifying which polynucleotide-corresponding oligonucleotide probes of said array are complementary to portions of a nucleic acid which binds to said given oligonucleotide polynucleotide-corresponding corresponding probe, thereby identifying which polynucleotides are complementary to said given nucleic acid, wherein said array of oligonucleotide probes is immobilized on a region of a combination, wherein said combination comprises
1) a surface comprising a number of spatially discrete, substantially identical, regions equal to the number of polynucleotides to be studied, each region comprising
2) a number of different anchors equal to the number of polynucleotides to be studied, each anchor in association with
3) a bifunctional linker which has a first portion that is specific for the anchor, and a second portion that comprises an oligonucleotide probe which corresponds to at least one of said polynucleotides.

In another aspect of the invention, the above methods to map ESTs or other polynucleotides further comprise removing unbound portions of the sample between one or more of the steps.

In another embodiment of the invention, one or more RNA targets of interest (e.g., mRNA, or other types of RNA) are converted into cDNAs by reverse transcriptase, and these cDNAs are then hybridized to a probe array. This type of assay is illustrated schematically in FIG. 8. RNA extracts (or purified mRNA) are prepared from cells or tissues as described herein. Reverse transcriptase and oligonucleotide primers which are specific for the RNAs of interest are then added to the RNA sample, and, using art-recognized conditions and procedures, which can be routinely determined and optimized, the first strands of cDNAs are generated. The term "specific" primer refers to one that is sufficiently complementary to an mRNA of interest to bind to it under selected stringent hybridization conditions and be recognized by reverse transcriptase, but which does not bind to undesired nucleic acid (see above for a discussion of appropriate reaction conditions to achieve specific hybridization). Residual RNA—mRNAs which were not recognized by the specific primers, and/or other types of contaminating RNAs in an RNA extract, such as tRNA or rRNA—can be removed by any of a variety of ribonucleases or by chemical procedures, such as treatment with alkali, leaving behind the single strand cDNA, which is subsequently placed in contact with a MAPS probe array. The use of reverse transcriptase in this method minimizes the need for extensive handling of RNA, which can be sensitive to degradation by nucleases and thus difficult to work with. Furthermore, the additional specificity engendered by the specific reverse transcriptase primers imparts an added layer of specificity to the assay.

Optionally, the cDNAs described above can be amplified before hybridization to the probe array to increase the signal strength. The oligonucleotide reverse transcriptase primers described above can comprise, at their 5' ends, sequences (which can be about 22–27 nucleotides long) that specify initiation sites for an RNA polymerase (e.g., T7, T3 or SP2 polymerase, or the like). In the example shown in FIG. 8, a T7 promoter sequence has been added to the reverse transcriptase primer. The polymerase recognition site becomes incorporated into the cDNA and can then serve as a recognition site for multiple rounds of transcription by the appropriate RNA polymerase (in vitro transcription, or IVT). Optionally, the mRNAs so generated can be amplified further, using PCR and appropriate primers, or the cDNA, itself, can be so amplified. Procedures for transcription and PCR are routine and well-known in the art.

The above-described method, in which mRNA targets are converted to cDNA with reverse transcriptase before assaying on MAPS plates, can be used instead of the standard MAPS assay procedure for any of the RNA-based assays described above.

In another embodiment of the invention, one or more nucleic acid targets of interest are hybridized to specific polynucleotide protection fragments and subjected to a nuclease protection procedure, and those protection fragments which have hybridized to the target(s) of interest are assayed on MAPS plates. If the target of interest is an RNA and the protection fragment is DNA, a Nuclease Protection/MAPS Assay (NPA-MAPS) can reduce the need for extensive handling of RNA, which can be sensitive to degradation by contaminating nucleases and thus difficult to work with. In such an NPA-MAPS assay, the probes in the probe array are oligonucleotides of the same strandedness as the nucleic acid targets of interest, rather than being complementary to them, as in a standard MAPS assay. One example of an NPA-MAPS assay is schematically represented in FIG. 9.

In an NPA-MAPS assay, the target of interest can be any nucleic acid, e.g., genomic DNA, cDNA, viral DNA or RNA, rRNA, tRNA, mRNA, oligonucleotides, nucleic acid fragments, modified nucleic acids, synthetic nucleic acids, or the like. In a preferred embodiment of the invention, the procedure is used to assay for one or more mRNA targets which are present in a tissue or cellular RNA extract. A sample which contains the target(s) of interest is first hybridized under selected stringent conditions (see above for a discussion of appropriate reaction conditions to achieve specific hybridization) to one or more specific protection fragment(s). A protection fragment is a polynucleotide, which can be, e.g., RNA, DNA (including a PCR product), PNA or modified or substituted nucleic acid, that is specific for a portion of a nucleic acid target of interest. By "specific" protection fragment, it is meant a polynucleotide which is sufficiently complementary to its intended binding partner to bind to it under selected stringent conditions, but which will not bind to other, unintended nucleic acids. A protection fragment can be at least 10 nucleotides in length, preferably 50 to about 100, or about as long as a full length cDNA. In a preferred embodiment, the protection fragments are single stranded DNA oligonucleotides. Protection fragments specific for as many as 100 targets or more can be included in a single hybridization reaction. After hybridization, the sample is treated with a cocktail of one or more nucleases so as to destroy substantially all nucleic acid except for the protection fragment(s) which have hybridized to the nucleic acid(s) of interest and (optionally) the portion(s) of nucleic acid target which have hybridized and been protected from nuclease digestion during the nuclease protection procedure (are in a duplexed hybrid). For example, if the sample comprises a cellular extract, unwanted nucleic acids, such as genomic DNA, tRNA, rRNA and mRNA's other than those of interest, can be substantially destroyed in this step. Any of a variety of nucleases can be used, including, e.g., pancreatic RNAse, mung bean nuclease, S1 nuclease, RNAse A, Ribonuclease T1, Exonuclease III, or the like, depending on the nature of the hybridized complexes and of the undesirable nucleic acids present in the sample. RNAse H can be particularly useful for digesting residual RNA bound to a DNA protection fragment. Reaction conditions for these enzymes are well-known in the art and can be optimized empirically. Also, chemical procedures can be used, e.g., alkali hydrolysis of RNA. As required, the samples can be treated further by well-known procedures in the art to remove unhybridized material and/or to inactivate or remove residual enzymes (e.g., phenol extraction, precipitation, column filtration, etc.). The process of hybridization, followed by nuclease digestion and (optionally) chemical degradation, is called a nuclease protection procedure; a variety of nuclease protection procedures have been described (see, e.g., Lee et al (1987). *Meth. Enzymol.* 152, 633–648. Zinn et al (1983). *Cell* 34, 865–879.). Samples treated by nuclease protection, followed by an (optional) procedure to inactivate nucleases, are placed in contact with a MAPS probe array and the usual steps of a MAPS assay are carried out. Bound protection fragments can be detected by hybridization to labeled target-specific reporters, as described herein for standard MAPS assays, or the protection fragments, themselves, can be labeled, covalently or non-covalently, with a detectable molecule.

In a preferred embodiment, the protection fragment is directly labeled, e.g., rather than being labeled by hybridization to a target-specific reporter. For example, the reporter is bound to the protection fragment through a ligand-antiligand interaction, e.g., a streptavidin enzyme complex is added to a biotinylated protection oligonucleotide. In another example, the protection fragment is modified chemically, (e.g., by direct coupling of horseradish peroxidase (HRP) or of a fluorescent dye) and this chemical modification is detected, either with the nucleic acid portion of the protection fragment or without it, (e.g., after cleavage of the modification by, for example, an enzymatic or chemical treatment). In any of the above methods, a protection fragment can be labeled before or after it has hybridized to a corresponding linker molecule.

In order to control that the nuclease protection procedure has worked properly, i.e. that non-hybridized nucleic acids have been digested as desired, one can design one or more protection fragments to contain overhanging (non-hybridizing) segments that should be cleaved by the nucleases if the procedure works properly. The presence or absence of the overhanging fragments can be determined by hybridization with a complementary, labeled, detection probe, or the overhanging portion of the protection fragment, itself, can be labeled, covalently or non-covalently, with a detectable molecule. This control can be performed before the sample is placed in contact with the probe array, or as a part of the MAPS assay, itself. An example of such a control assay is described in Example 15.

Of course, because different labels can be easily distinguished (e.g., fluors with different absorption spectra), several differently labeled oligonucleotides can be included in a single assay. Further, the standard nuclease protection assay as analyzed by gel electrophoresis can be used during assay development to verify that the protection fragments are processed as expected.

NPA-MAPS assays can be used to quantitate the amount of a target in a sample. If protection fragment is added at a large enough molar excess over the target to drive the hybridization reaction to completion, the amount of protection fragment remaining after the nuclease protection step will reflect how much target was present in the sample. One example of such a quantitation reaction is described in Examples 12 and 13.

NPA-MAPS assays can be used to implement any of the methods described above that use standard MAPS assays.

In a preferred embodiment, the polynucleotide protection fragments are measured by the mass spectrometer rather than on MAPS plates. In a most preferred embodiment, none of the polynucleotides are bound (attached) to a solid surface during the hybridization or nuclease digestion steps. After hybridization, the hybridized target can be degraded, e.g., by nucleases or by chemical treatments, leaving the protection fragment in direct proportion to how much fragment had been hybridized to target. Alternatively, the sample can be treated so as to leave the (single strand) hybridized portion of the target, or the duplex formed by the hybridized target and the protection fragment, to be further analyzed. The samples to be analyzed are separated from the rest of the hybridization and nuclease mixture (for example by ethanol precipitation or by adsorption or affinity chromatography, etc.), eluted or solubilized, and injected into the mass spectrometer by loop injection for high throughput. In a preferred embodiment, the samples to be analyzed (e.g., protection fragments) are adsorbed to a surface and analyzed by laser desorption, using well-known methods in the art. For highest sensitivity Fourier Transform Mass Spectrometry (FTMS) (or other similar advanced technique) may be used, so that femtomoles or less of each protection fragment can be detected.

The protection fragments that are to be detected within one (or more) samples can be designed to give a unique signal for the mass spectrometer used. In one embodiment, the protection fragments each have a unique molecular weight after hybridization and nuclease treatment, and their molecular weights and characteristic ionization and fragmentation pattern will be sufficient to measure their concentration. To gain more sensitivity or to help in the analysis of complex mixtures, the protection fragments can be modified (e.g., derivatized) with chemical moieties designed to give clear unique signals. For example each protection fragment can be derivatized with a different natural or unnatural amino acid attached through an amide bond to the oligonucleotide strand at one or more positions along the hybridizing portion of the strand. With a mass spectrometer of appropriate energy, fragmentation occurs at the amide bonds, releasing a characteristic proportion of the amino acids. This kind of approach in which chemical moieties of moderate size (roughly 80 to 200 molecular weight) are used as mass spectrometric tags is desirable, because molecules of this size are generally easier to detect. In another example, the chemical modification is an organic molecule with a defined mass spectrometric signal, such as a tetraalkylammonium group which can, for example, derivatize another molecule such as, e.g., an amino acid. In another example, positive or negative ion signals are enhanced by reaction with any of a number of agents. For example, to enhance positive ion detection, one can react a pyrylium salt (such as, e.g., 2–4-dithenyl, 6-ethyl pyrylium tetrafluoroborate, or many others) with an amine to form a pyridinium salt; any of a number of other enhancing agents can be used to form other positively charged functional groups (see, e.g., Quirke et al (1994). *Analytical Chemistry* 66, 1302–1315). Similarly, one can react any of a number of art-recognized agents to form negative ion enhancing species. The chemical modification can be detected, of course, either after having been cleaved from the nucleic acid, or while in association with the nucleic acid. By allowing each protection fragment to be identified in a distinguishable manner, it is possible to assay (e.g., to screen) for a large number of different targets (e.g., for 2, 6, 10, 16 or more different targets) in a single assay. Many such assays can be performed rapidly and easily. Such an assay or set of assays can be conducted, therefore, with high throughput as defined herein.

Regardless of whether oligonucleotides are detected directly by their mass or if unique molecular tags are used, the signals for each molecule to be detected can be fully characterized in pure preparations of known concentration. This will allow for the signal to be quantified (measured, quantitated) accurately. For any molecule to be detected by mass spectrometry, the intensity and profile cannot be predicted with accuracy. The tendency of the molecule to be ionized, the sensitivity of all chemical bonds within the molecule to fragmentation, the degree to which each fragment is multiply charged or singly charged, are all too complex to be predicted. However, for a given instrument with fixed energy and sample handling characteristics the intensity and profile of the signal is very reproducible. Hence for each probe the signal can be characterized with pure standards, and the experimental signals interpreted quantitatively with accuracy.

In one aspect, the invention relates to a method to detect one or more nucleic acids of interest, comprising subjecting a sample comprising the nucleic acid(s) of interest to nuclease protection with one or more protection fragments, and detecting the hybridized duplex molecules, or the protected nucleic acid, or the protection fragment, with mass spectrometry.

Methods of analyzing nucleic acids by mass spectrometry are well-known in the art. See, e.g., Alper et al (1998). *Science* 279, 2044–2045 and Koster, U.S. Pat. No. 5,605, 798.

In addition to the variety of high throughput assays described above, many others will be evident to one of skill in the art.

An advantage of using multiprobe assays is the ability to include a number of "control" probes in each probe array which are subject to the same reaction conditions as the actual experimental probes. For example, each region in the array can comprise positive and/or negative controls. The term, a "positive control probe," is used herein to mean a control probe that is known, e.g., to interact substantially with the target, or to interact with it in a quantitatively or qualitatively known manner, thereby acting as a(n internal) standard for the probe/target interaction. Such a probe can control for hybridization efficiency, for example. The term, a "negative control probe," is used herein to mean a control probe which is known not to interact substantially with the target. Such a probe can control for hybridization specificity, for example. As examples of the types of controls which can be employed, consider an assay in which an array of oligonucleotide probes is used to screen for agents which modulate the expression of a set of correlative genes for a disease. As an internal normalization control for variables such as the number of cells lysed for each sample, the recovery of mRNA, or the hybridization efficiency, a probe array can comprise probes which are specific for one or more basal level or constitutive house-keeping genes, such as structural genes (e.g., actin, tubulin, or others) or DNA binding proteins (e.g., transcription regulation factors, or others), whose expression is not expected to be modulated by the agents being tested. Furthermore, to determine whether the agents being tested result in undesired side effects, such as cell death or toxicity, a probe array can comprise probes which are specific for genes that are known to be induced as part of the apoptosis (programmed cell death) process, or which are induced under conditions of cell trauma (e.g., heat shock proteins) or cell toxicity (e.g., p450 genes).

Other control probes can be included in an array to "fine tune" the sensitivity of an assay. For example, consider an assay for an agent which modulates the production of mRNAs associated with a particular disease state. If previous analyses have indicated that one of the correlative mRNAs (say, mRNA-A) in this set is produced in such high amounts compared to the others that its signal swamps out the other mRNAs, the linkers can be adjusted to "fine tune" the assay so as to equalize the strengths of the signals. "Blocked linkers," which comprise the anchor-specific oligonucleotide sequence designated for the mRNA-A target, but which lack the probe-specific sequence, can be added to dilute the pool of target-specific linkers and thus to reduce the sensitivity of the assay to that mRNA. The appropriate ratios of blocked and unblocked linkers can be determined with routine, conventional methods by one of skill in the art.

Samples to be tested in an assay of the invention can comprise any of the targets described above, or others. Liquid samples to be assayed can be of any volume appropriate to the size of the test region, ranging from about 100 nanoliters to about 100 microliters. In a preferred embodiment, liquid drops of about 1 microliter are applied to each well of a 1536 well microtiter dish. Samples can be placed in contact with the probe arrays by any of a variety of methods suitable for high throughput analysis, e.g., by pipetting, inkjet based dispensing or by use of a replicating pin tool. Samples are incubated under conditions (e.g., salt concentration, pH, temperature, time of incubation, etc.— see above) effective for achieving binding or other stable interaction of the probe and the target. These conditions are routinely determinable. After incubation, the samples can optionally be treated (e.g., washed) to remove unbound target, using conditions which are determined empirically to leave specific interactions intact, but to remove non-specifically bound material. For example, samples can be washed between about one and ten times or more under the same or somewhat more stringent conditions than those used to achieve the probe/target binding.

Samples containing target RNA, e.g., mRNA, rRNA, tRNA, viral RNA or total RNA, can be prepared by any of a variety of procedures. For example, in vitro cell cultures from which mRNA is to be extracted can be plated on the regions of a surface, such as in individual wells of a microtiter plate. Optionally, these cells, after attaining a desired cell density, can be treated with an agent of interest, such as a stimulating agent or a potential therapeutic agent, which can be added to the cells by any of a variety of means, e.g., with a replicating pin tool (such as the 96 or 384 pin tools available from Beckman), by pipetting or by ink-jet dispensing, and incubated with the cells for any appropriate time period, e.g., between about 15 minutes and about 48 hours, depending upon the assay. Total RNA, mRNA, etc. extracts from tissues or cells from an in vitro or in vivo source can be prepared using routine, art-recognized methods (e.g., commercially available kits).

Optionally, nucleic acid which might compete with an RNA of interest for hybridization to a specific probe (i.e. genomic DNA, rRNA, tRNA or mRNA which shares at least partial sequence homology with the RNA of interest) can be at least partially removed from an RNA sample by pretreating the sample with a nuclease protection (NP) procedure before subjecting it to hybridization. A nucleic acid (a "protection fragment," which can be, e.g., RNA, DNA or PNA), which is complementary to at least a portion of the RNA of interest and whose sequence partially or completely overlaps that of the probe which is specific for the RNA of interest, is introduced in excess into the sample and incubated with it under selected stringent hybridization conditions in which the protection fragment hybridizes specifically to the RNA of interest (see above for a discussion of appropriate reaction conditions). At this step, protection fragments specific for any or all of the RNAs of interest in the sample can be added (e.g., as many as 100, or more). After hybridization, the sample is treated with a cocktail of one or more nucleases so as to destroy substantially all nucleic acid except for the portions of each RNA of interest which are complementary to the protection fragments(s), or except for the duplexes formed between the protection fragment(s) and the protected RNA. In a subsequent step, the protection fragment(s) can be eliminated from such duplexes by denaturing the duplexes and digesting with an appropriate enzyme which will degrade protection fragment (s), leaving the protected RNA substantially intact. Any of a variety of nucleases can be used for the above-discussed digestion steps, including, e.g., pancreatic RNAse, mung bean nuclease, RNAse H, S1 nuclease (under digestion conditions with either high or low salt), RNAse A, Ribonuclease TI, Exonuclease III, Exonuclease VII, RNAse CL3, RNAse PhyM, Rnase U2, and the like, depending on the nature of the hybridized complexes and of the undesirable nucleic acids present in the sample. Reaction conditions for these enzymes are well-known in the art and can be optimized empirically. As required, the samples can be treated by well-known procedures in the art to remove unhybridized material and/or to inactivate or remove residual enzymes (e.g., phenol extraction, precipitation, column filtration, etc.). The treated samples are then placed in contact with the probe array. In order to control that specific hybridization and subsequent nuclease protection has occurred properly, one can include labeled protection fragments in the reaction mixture. In order to control that the nuclease protection procedure has worked properly, i.e. that non-hybridized nucleic acids has been digested as desired, one can design one or more protection fragments to contain overhanging (non-hybridizing) segments that should be cleaved by the nucleases if the assay works properly. The presence or absence of the overhanging fragments can be determined by hybridization with a complementary, labeled probe, or the overhanging portion of the protection fragment, itself, can be labeled with a detectable molecule.

For any of the methods of this invention, targets can be labeled (tagged) by any of a variety of procedures which are well-known in the art and/or which are described elsewhere herein (e.g., for the detection of nuclease protection fragments). For example, the target molecules can be coupled directly or indirectly with chemical groups that provide a signal for detection, such as chemiluminescent molecules, or enzymes which catalyze the production of chemiluminsecent molecules, or fluorescent molecules like fluorescein or cy5, or a time resolved fluorescent molecule like one of the chelated lanthanide metals, or a radioactive compound. Alternatively, the targets can be labeled after they have reacted with the probe by one or more target-specific reporters (e.g., antibodies, oligonucleotides as shown in FIG. 1, or any of the general types of molecules discussed above in conjunction with probes and targets). A variety of more complex sandwich-type detection procedures can also be employed. For example, a target can be hybridized to a bifunctional molecule containing a first moiety which is specific for the target and a second moiety which can be recognized by a common (i.e., the same) reporter reagent, e.g., a labeled polynucleotide, antibody or the like. The bifunctional molecules can be designed so that any desired number of common reporters can be used in each assay.

Methods by which targets can be incubated with a target-specific reporter(s) under conditions effective for achieving binding or other stable interaction are routinely determinable (see above). For example, fluorescent oligonucleotide reporters (at a concentration of about 10 nM to about 1 $\mu$M or more, preferably about 30 nM, in a buffer such as 6×SSPE-T or others) can be incubated with the bound targets for between about 15 minutes to 2 hours or more (preferably about 30 to 60 minutes), at a temperature between about 15° C. and about 45° C. (preferably about room temperature). After incubation, the samples can optionally be treated (e.g., washed) to remove unbound target-specific reporters, using conditions which are determined empirically to leave specific interactions intact, but to remove non-specifically bound material. For example, samples can be washed between about one and ten times or more under the same or somewhat more stringent conditions than those used to achieve the target/reporter binding.

Tagging with a target-specific reporter(s) can provide an additional layer of specificity to the initial hybridization reaction, e.g., in the case in which a target-specific oligonucleotide reporter is targeted to a different portion of the sequence of a target nucleic acid than is the probe oligonucleotide, or in which probe and reporter antibodies recognize different epitopes of a target antigen. Furthermore, tagging with target-specific reporters can allow for "tuning" the sensitivity of the reaction. For example, if a target mRNA which is part of a correlative expression pattern is expressed at very low levels, the level of signal can be enhanced (signal amplification) by hybridizing the bound target to several (e.g., about two to about five or more) target-specific oligonucleotide reporters, each of which hybridizes specifically to a different portion of the target mRNA.

The ability to detect two types of labels independently allows for an additional type of control in MAPS assays. Some (e.g., about 10 to about 100%) of the linkers designated for a particular anchor locus (FIG. 7 shows 3 typical anchor loci, each comprising a plurality of substantially identical anchors (A, B or C)) can have a label (e.g., a fluor) attached to one end. For example, a rhodamine or Cy5 fluor can be attached at the 5' end of the linker. Such modified linkers are termed "control linkers." After a mixture of linkers and control linkers has been associated with anchors and a sample containing a target has been incubated with the resulting probe array, a target-specific reporter bearing a different fluor (e.g., fluorescein or another detection label such as a chemiluminescent one) can be used (or the target can be directly labeled with a fluor or other detection label); and the ratio of the two signals can be determined. The presence of control linkers permits calibration of the number of functional (e.g., able to interact with linkers) anchors within and between test regions (i.e. tests the capacity of each locus of the array to bind target, for purposes of normalizing signals), serves as a basis for quantitation of the amount of bound target, aids in localization of the anchor loci and/or provides a positive control, e.g., in cases in which there is no signal as a result of absence of target in a sample. In one embodiment of the invention, two different labels (e.g., fluorophores) can also be used to detect two different populations of target molecules; however, the ability to recognize the presence of targets by spatial resolution of signals allows the use of a single type of label for different target molecules.

In another embodiment of the invention, "anchors" which are specific for a target(s) of interest are not associated with linkers, but rather are associated directly with the target(s); the target(s), in turn, can interact optionally with a target-specific reporter(s).

Targets, whether labeled or unlabeled, can be detected by any of a variety of procedures, which are routine and conventional in the art (see, e.g., Fodor et al (1996). U.S. Pat. No. 5,510,270; Pirrung et al (1992). U.S. Pat. No. 5,143,854; Koster (1997). U.S. Pat. No. 5,605,798; Hollis et al (1997) U.S. Pat. No. 5,653,939; Heller (1996). U.S. Pat. No. 5,565,322; Eggers et al (1997). U.S. Pat. No. 5,670,322; Lipshutz et al (1995). *BioTechniques* 19, 442–447; Southern (1996). *Trends in Genetics* 12, 110–115). Detection methods include enzyme-based detection, calorimetric methods, SPA, autoradiography, mass spectrometry, electrical methods, detection of absorbance or luminescence (including chemiluminescence or electroluminescence), and detection of light scatter from, e.g., microscopic particles used as tags. Also, fluorescent labels can be detected, e.g., by imaging with a charge-coupled device (CCD) or fluorescence microscopy (e.g., scanning or confocal fluorescence microscopy), or by coupling a scanning system with a CCD array or photomultiplier tube, or by using array-based technology for detection (e.g., surface potential of each 10-micron part of a test region can be detected or surface plasmon resonance can be used if resolution can be made high enough.) Alternatively, an array can contain a label (e.g., one of a pair of energy transfer probes, such as fluorescein and rhodamine) which can be detected by energy transfer to (or modulation by) the label on a linker, target or reporter. Among the host of fluorescence-based detection systems are fluorescence intensity, fluorescence polarization (FP), time-resolved fluorescence, fluorescence resonance energy transfer and homogeneous time-released fluorescence (HTRF). Analysis of repeating bar-code-like patterns can be accomplished by pattern recognition (finding the appropriate spot or line for each specific labeled target by its position relative to the other spots or lines) followed by quantification of the intensity of the labels. Bar-code recognition devices and computer software for the analysis of one or two dimensional arrays are routinely generated and/or commercially available (e.g., see Rava et al (1996). U.S. Pat. No. 5,545,531).

Methods of making and using the arrays of this invention, including preparing surfaces or regions such as those described herein, synthesizing or purifying and attaching or assembling substances such as those of the anchors, linkers, probes and detector probes described herein, and detecting and analyzing labeled or tagged substances as described herein, are well known and conventional technology. In addition to methods disclosed in the references cited above, see, e.g., patents assigned to Affymax, Affymetrix, Nanogen, Protogene, Spectragen, Millipore and Beckman (from whom products useful for the invention are available); standard textbooks of molecular biology and protein science, including those cited above; and Cozette et al (1991). U.S. Pat. No. 5,063,081; Southern (1996), Current Opinion in Biotechnology 7, 85–88; Chee et al (1996). Science 274, 610–614; and Fodor et al (1993). Nature 364, 555–556.

BRIEF DESCRIPTION OF THE DRAWINGS

FIG. 5a represents a well separator; FIG. 5b represents a subdivider; and FIG. 5c represents a base.

After washing, a single detector oligonucleotide is added to each well, as numbered in the figure. That is, the detector oligonucleotide with sequences complementary to the first EST is added to the first well, and so on.

Figure 18:
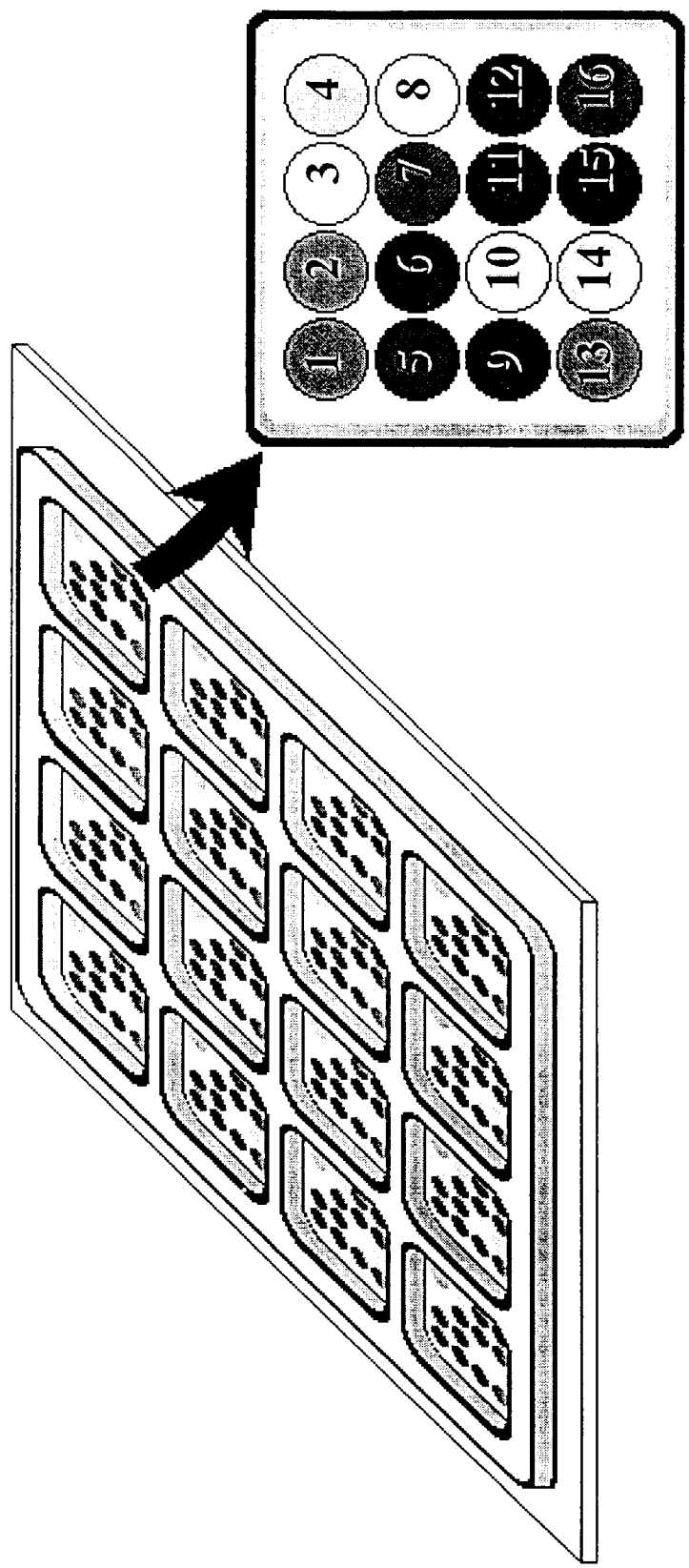
FIG. 18 illustrates the first step in an assay to map ESTs: assembling linkers corresponding to each of the ESTs to be mapped on arrays of generic anchors on a MAPS plate. To the surface of each of 16 wells of a microplate are attached linkers comprising 16 different oligonucleotide probes, arranged in a 4×4 matrix. The first locus has oligo 1, which is complementary to a portion of the first EST sequence, and so on for the 16 ESTs to be tested. cDNAs or mRNAs generated from the genes from which the ESTs were obtained are added to all 16 wells and allowed to hybridize under appropriate conditions. Hence, any cDNA or mRNA that contains one of the 16 EST sequences will be assembled at the locus where its complementary probe was placed.
Figure 19:
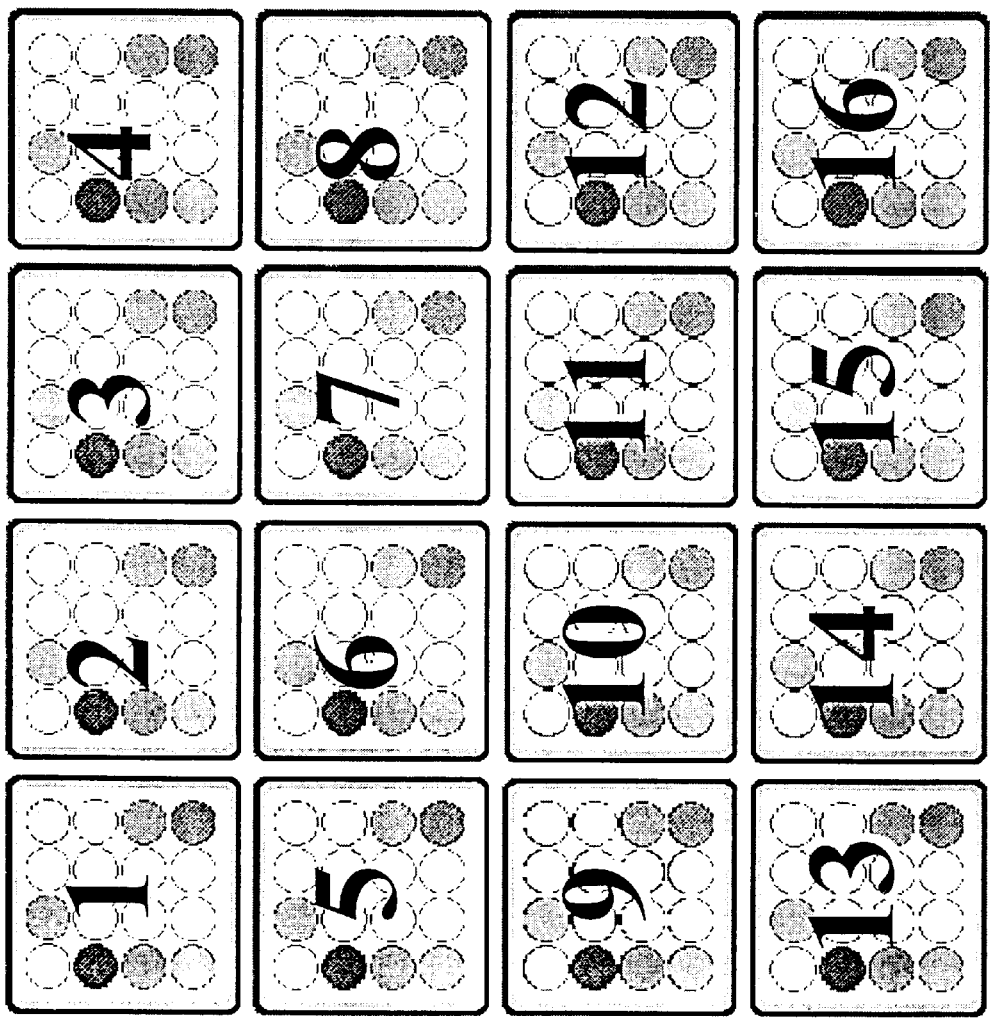
FIG. 19 illustrates a subsequent step in an assay to map ESTs: adding detector oligonucleotides to the MAPS plate. Each well of the plate receives a detector oligonucleotide which corresponds to one of the ESTs to be mapped. Each detector oligonucleotide is an oligonucleotide coupled to a molecule used for detection, e.g., fluorescein if fluorescence imaging is to be the method of detection. Each detector oligonucleotide is complementary to one of the ESTs, but different from the EST-specific probe, so that a probe and a detector oligonucleotide which are complementary to a single EST can both bind at the same time.
Figure 20A:
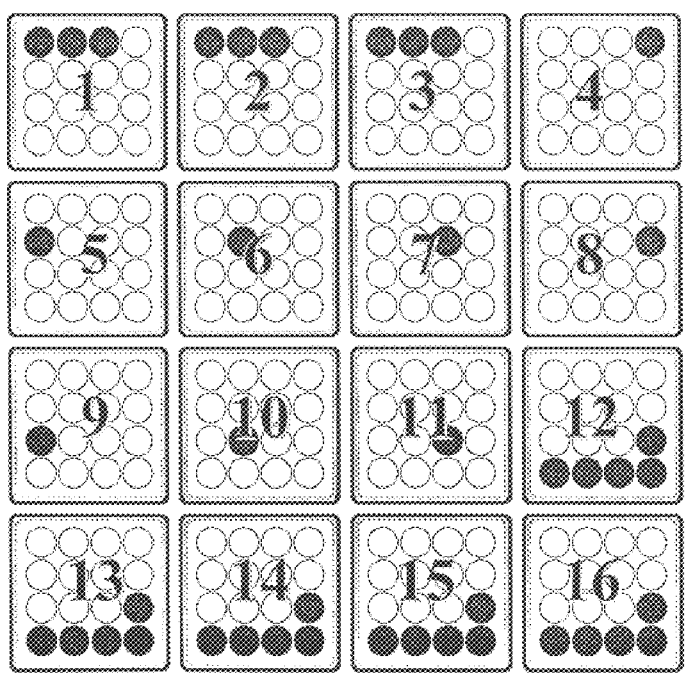
Figure 20B:
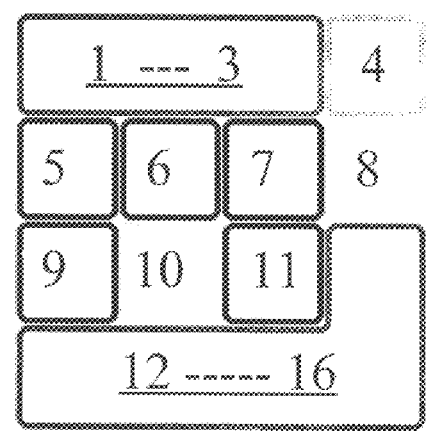

FIGS. 20a and b illustrate the results of the assay to map ESTs shown in FIGS. 18 and 19. After hybridization of detector oligonucleotides and washing with appropriate conditions of stringency, the 16 wells of the microplate are imaged with a CCD-based fluorescence imager, for example. FIG. 20a shows stylized results. It is expected that each EST-specific detector oligonucleotide should label the mRNA or cDNA held down by the corresponding EST-specific probe. For example, probe 5 assembles the cDNA or mRNA containing the fifth EST sequence at that locus, so the fifth detector oligonucleotide should also hybridize to the cDNA or mRNA at the same locus. This is the case for these stylized data, with each detection oligonucleotide labeling the matching probe. In addition, the first three detector oligonucleotides each label cDNA or mRNA held down by the first three probes, showing that these sequences lie along the same gene. Similarly, the last five ESTs appear to be linked. The linkage assigned from these data are presented graphically in FIG. 20b.

Figure 21:
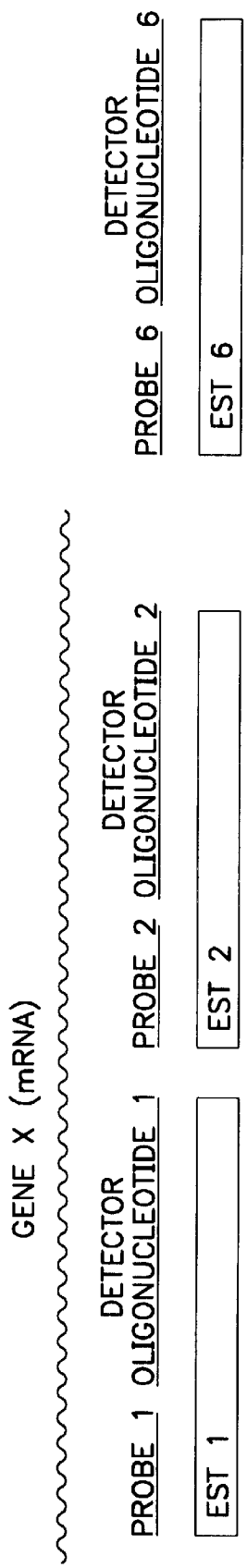

FIG. 21 illustrates the relationships of the probes, detector oligonucleotides and ESTs #1, 2 and 6 shown in FIGS. 18–20.

Figure 22:
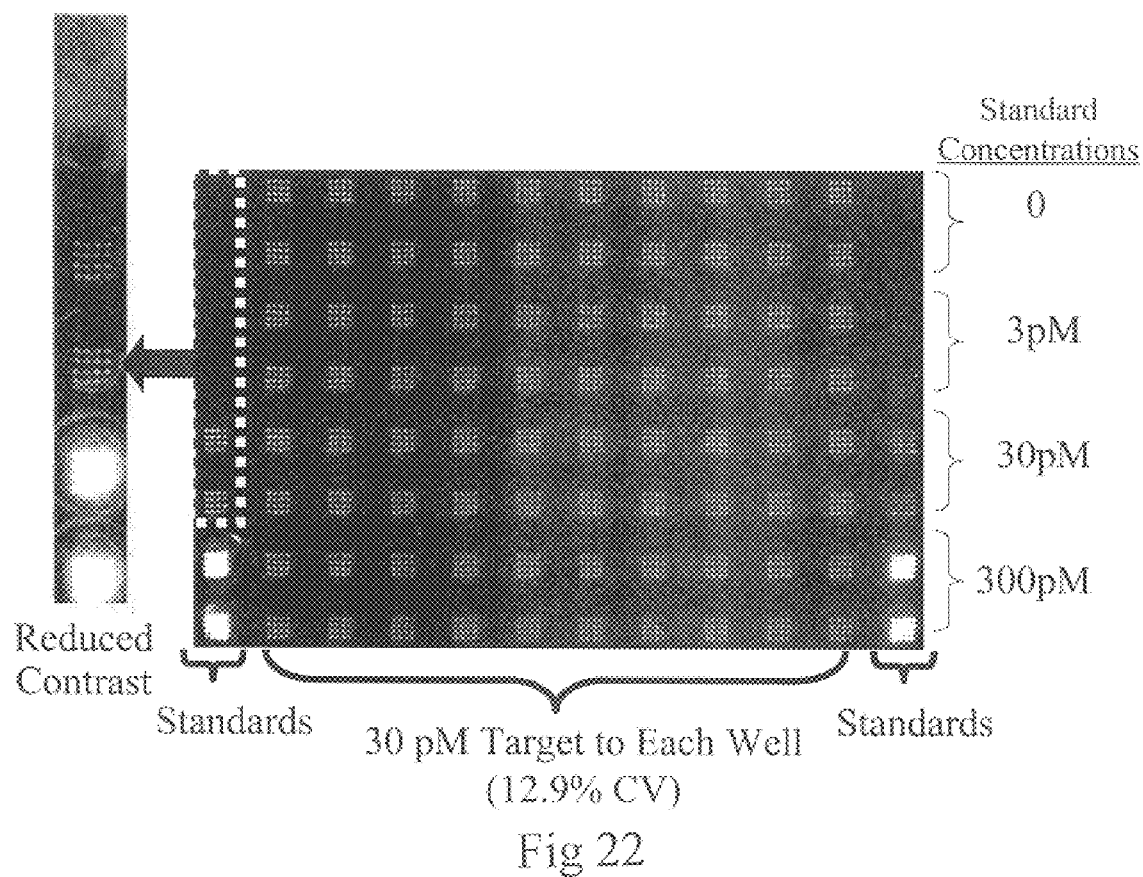

FIG. 22 illustrates a high throughput assay.

EXAMPLES

Figure 10:
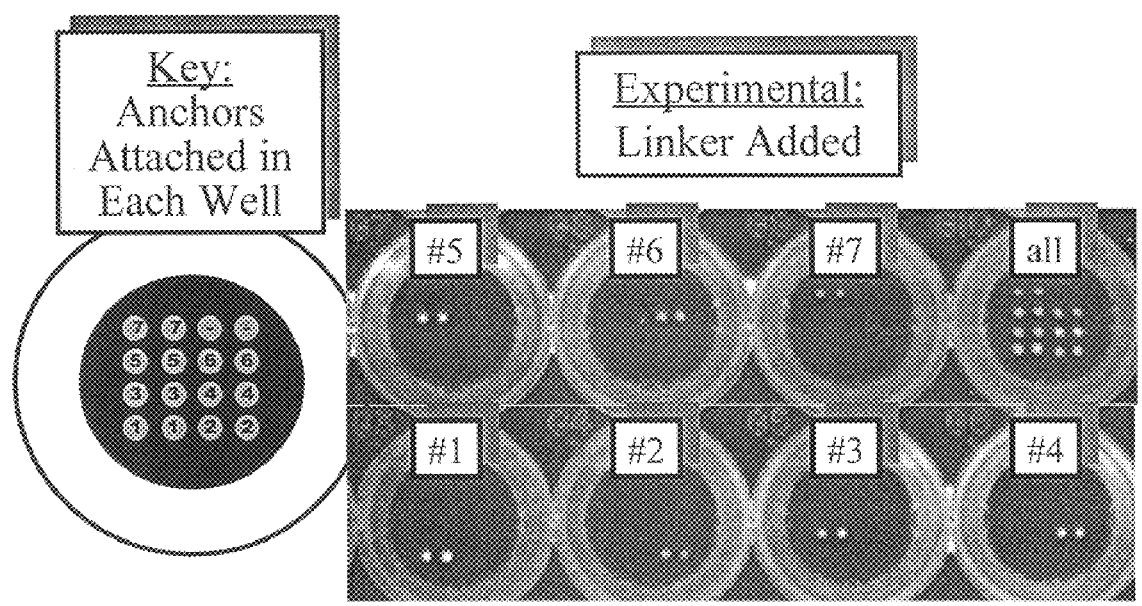
FIG. 10 illustrates hybridization specificity in a MAPS assay.

Example 1
Hybridization Specificity (see FIG. 10)

A generic MAPS plate was produced by using an inkjet dispenser, the Pixus system (Cartesian Technologies, Inc., Irvine, Calif.) to form an identical grid of DNA within each well of a microtiter plate. All oligonucleotides were purchased from Biosource International (Camarillo, Calif.). For this plate, seven different oligonucleotide anchors were dispensed within each well in the pattern shown as the Key (left side of the figure). Each oligonucleotide was dispensed as a 10 nanoliter droplet to two spots, from a 2 uM solution containing 500 mM sodium phosphate pH 8.5 and 1 mM EDTA to the wells of a DNA Bind plate (Corning Costar), and allowed to dry. After attachment, wells were blocked with 50 mM Tris pH 8, and then oligonucleotide that had not covalently attached to the surface was washed away with 0.1% SDS in 5×SSP buffer.

To the washed plate fluorescently labeled linker oligonucleotides were added and allowed to hybridize in 6×SSPE with 0.1% Triton X-100 at room temperature for thirty minutes. This is a preferred protocol for attachment of linkers. The linker oligonucleotides were cy5-derivatized during synthesis, and were complementary in 25 base-pair segments to specific anchoring oligonucleotides. The sequences of the seven anchors and linkers were as follows (all shown 3' to 5'):

```
#1 Anchor*:                                                              SEQ ID:1
      TCCACGTGAGGACCGGACGGCGTCC
   Linker**                                                              SEQ ID:2
      GTCGTTTCCATCTITGCAGTCATAGGATACTGAGTGGACGCCGTCCGGTCCTCACGTG
      GA
   RNA mimic(mouse C-jun):                                               SEQ ID:3
      CTATGACTGCAAAGATGGAAACGACGATACTGAGTTGGACCTAACATTCGATCTCATTCA
   Detector Oligonucleotide***                                           SEQ ID:4
      TGAATGAGATCGAATGTTAGGTCCA

#2 Anchor*:                                                              SEQ ID:5
      CACTACGGCTGAGCACGTGCGCTGC
   Linker**                                                              SEQ ID:6
      CTAGGCTGAAGTGTGGCTGGAGTCTGCAGCGCACGTGCTCAGCCGTAGTG
   RNA mimic (mouse MFP-2):                                              SEQ ID:7
      AGACTCCAGCCACACTTCAGCCTAGGATACTGAGTCTGAACAAAGGCAAGGCTAACT
      GAC
   Detector Oligonucleotide***                                           SEQ ID:8
      GTCAGTTAGCCTTGCCTTTGTTCAG

#3 Anchor*:                                                              SEQ ID:9
      GTCAGTTAGCCTTGCCTTTGTTCAG
   Linker**                                                              SEQ ID:10
      ACCATGTAGTTGAGGTCAATGAAGGGCGCTCCCACAACGCTCGACCGGCG
   RNA mimic (mouse GAPDH):                                              SEQ ID:11
      CCTTCATTGACCTCAACTACATGGTGATACTGAGTGGAGAAACCTGCCAAGTATGATG
      AC
   Detector Oligonucleotide***                                           SEQ ID:12
      GTCATCATACTTGGCAGGTFTCTCC

#4 Anchor*:                                                              SEQ ID:13
      GAACCGCTCGCGTGTTCTACAGCCA
   Linker**                                                              SEQ ID:14
      CTACCGAGCAAACTGGAAATGAAATTGGCTGTAGAACACGCGAGCGGTTC
   RNA mimic (mouse L32 protein):                                        SEQ ID:15
      ATTTCATTFCCAGTTTGCTCGGTAGGATACTGAGTGAGTCACCAATCCCAACGCCAGG
      CT
   Detector Oligonucleotide***                                           SEQ ID:16
      AGCCTGGCGTTGGGATTGGTGACTC

#5 Anchor*:                                                              SEQ ID:17
      CTCGTTCCGCGTCCGTGGCTGCCAG
   Linker**                                                              SEQ ID:18
      CTGGCAGCCACGGACGCGGAACGAG
#6 Anchor*:                                                              SEQ ID:19
      CGGTCGGCATGGTACCACAGTCCGC
   Linker**                                                              SEQ ID:20
      GCGGACTGTGGTACCATGCCGACCG

#7 Anchor*:                                                              SEQ ID:21
      GCGCGCCGCGTTATGCATCTCTTCG
   Linker**                                                              SEQ ID:22
      CGAAGAGATGCATAACGCGGCGCCG
```

*Anchors were synthesized with C12 spacer with amide at the 5' end
**Linkers were synthesized with Cy5 attached at the 5' end
***Detector Oligonucleotides were synthesized with biotin attached at the 5' end To each well either one linker or a mixture of linkers (as indicated in the figure) was added in bulk. (To the well marked "all" was added a mixture of all seven linkers.) Following incubation and washing in 5×SSP 3 times, the fluorescence picture shown on the right portion of the figure was taken with a Tundra imager (IRI, St. Catherines, Ontario). As can be seen, the linkers self-assembled to the surface, by specifically associating with their complementary anchors.

This process is repeated except that eight different anchors are dispersed in each well and linkers subsequently preferentially associated therewith. The entire process is repeated with 36, 64 etc. different anchors in each well of a 24, 96, 384, 864 or 1536 well plate.

Example 2

Figure 11:
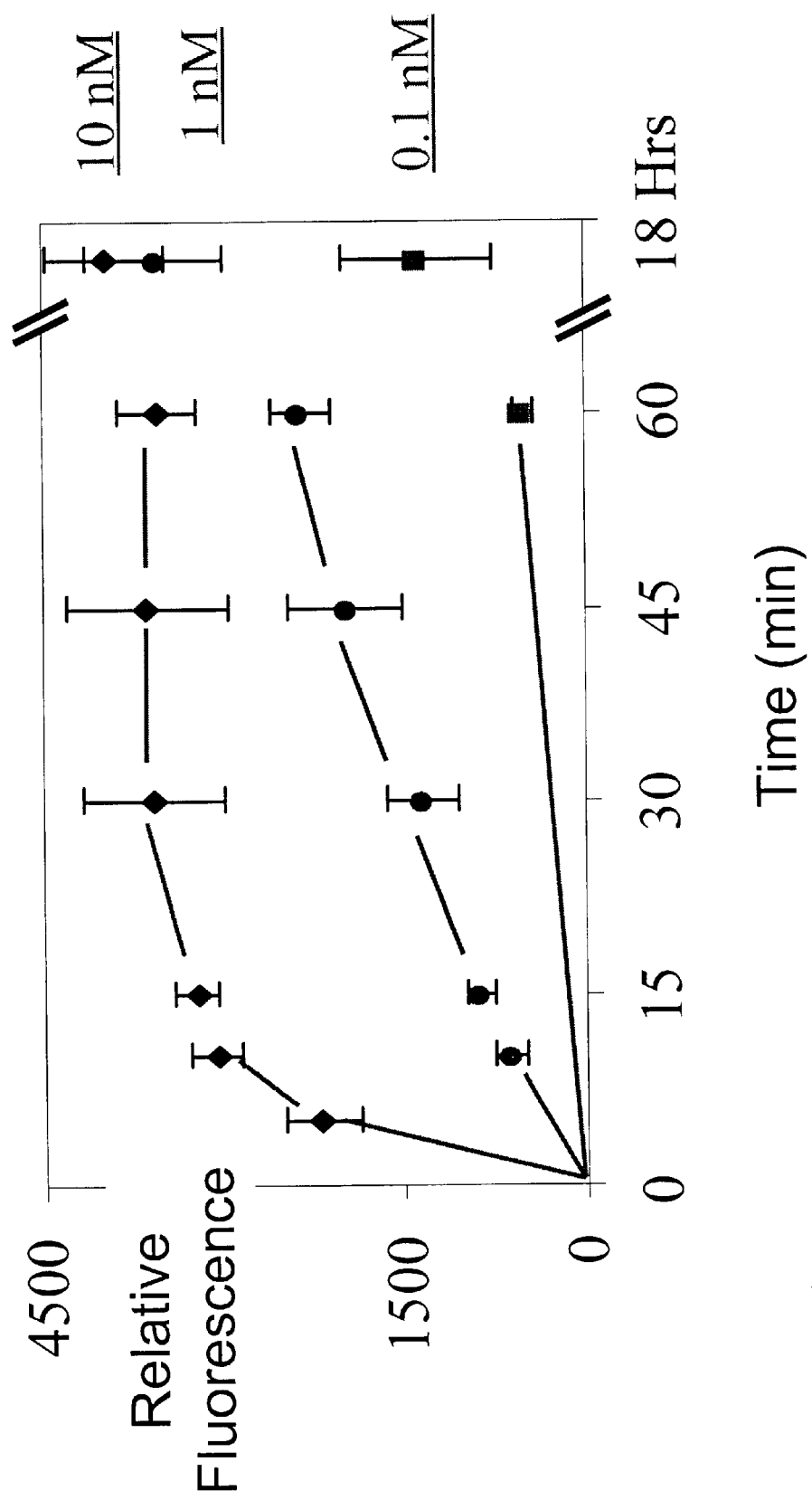
FIG. 11 illustrates binding kinetics of an anchor to a linker.

Binding Kinetics (see FIG. 11)

Figure 1:
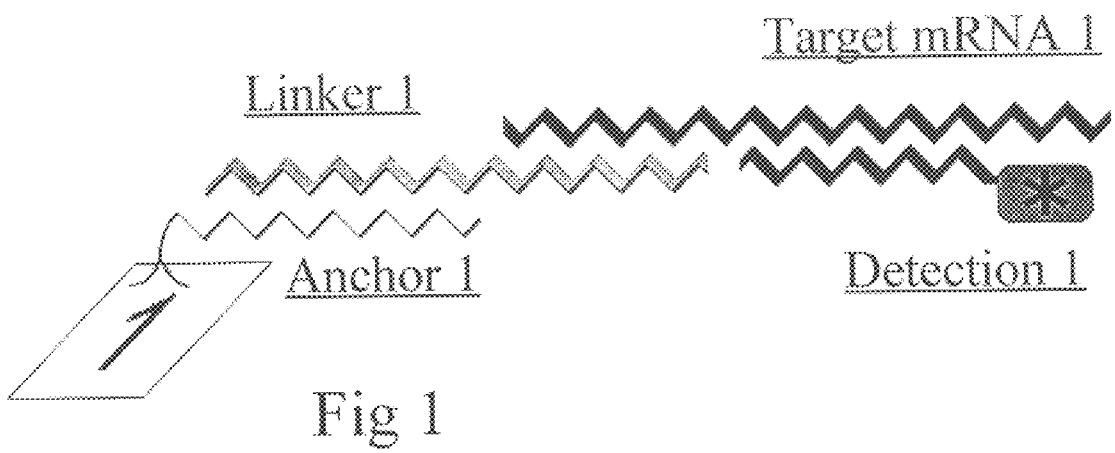
FIG. 1 illustrates a design scheme for oligonucleotides, in which a linker 1 contains a portion that is specific for anchor 1 and another portion (a probe) that is specific for target mRNA 1, and in which a labeled detection probe 1 is specific for a sequence of target mRNA 1 which is different from the sequence of the target-specific portion of the linker.
Figure 2:
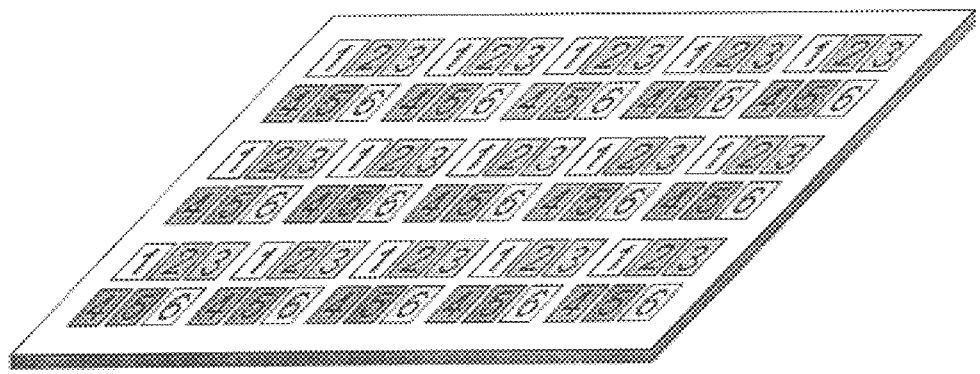
FIG. 2 illustrates a surface which comprises 15 test regions, each of which comprises an array of six anchor oligonucleotides.
Figure 3:
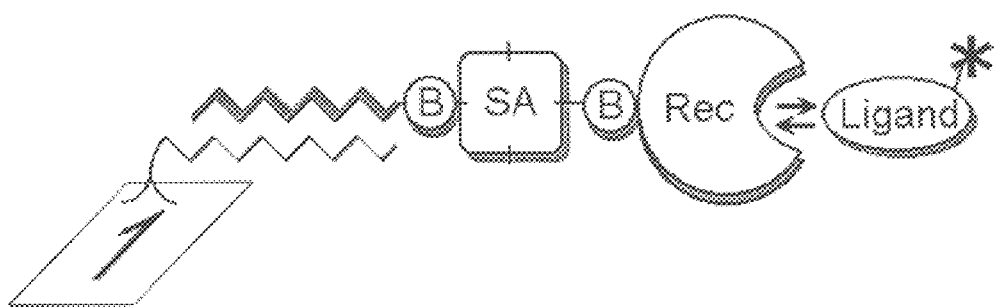
FIG. 3 illustrates the design of a linker for a receptor binding assay, in which the anchor-specific portion of the linker is associated with the probe portion (the receptor protein) via biotin and streptavidin molecules, and in which a ligand specific for the receptor is labeled with a fluorescent labeling molecule. B: Biotin. SA: Streptavidin. Rec: Receptor protein. Ligand: a natural or synthetic ligand for the receptor. *: a fluorescent labeling molecule attached to the Ligand.
Figure 4:
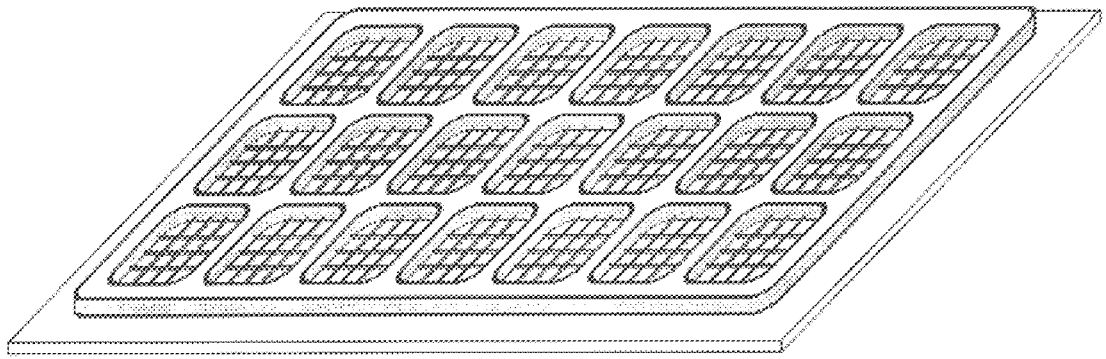
FIG. 4 illustrates a surface which comprises 21 test regions, each of which is further subdivided into 16 subregions (indentations, dimples).
Figure 5A:
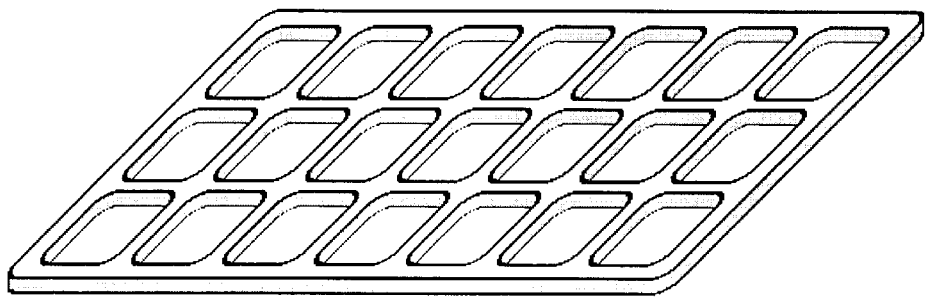
FIGS. 5a, 5b and 5c illustrate three pieces from which a surface such as that shown in FIG. 4 can be assembled.
Figure 5B:
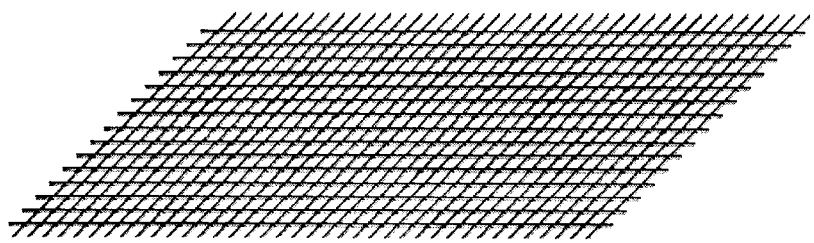
Figure 5C:
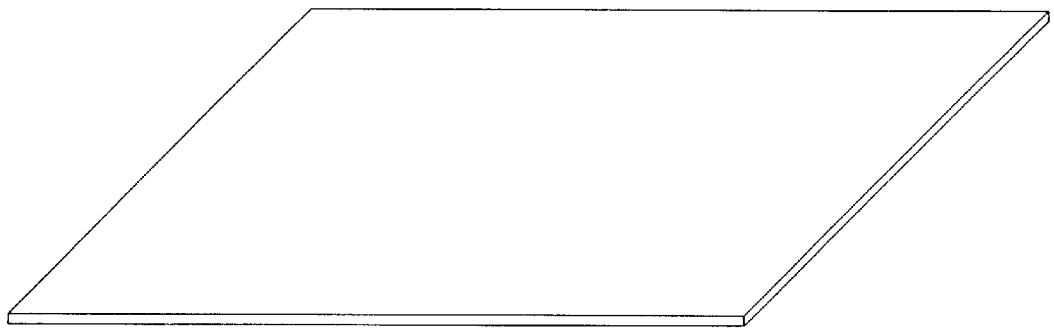
Figure 6:
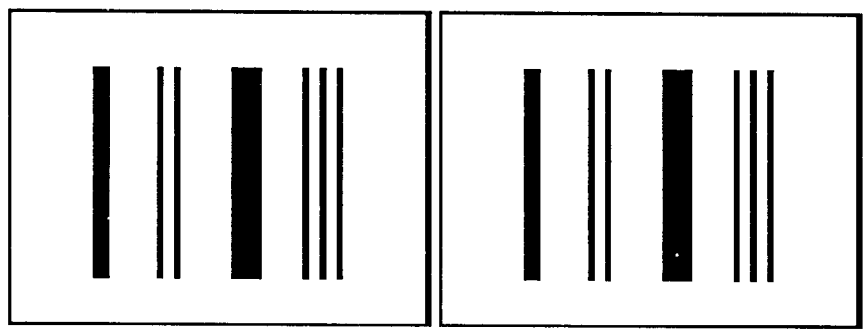
FIG. 6 represents two test regions, each of which comprises a linear array of probes (or anchors) which are in a "bar-code"-like formation.
Figure 7:
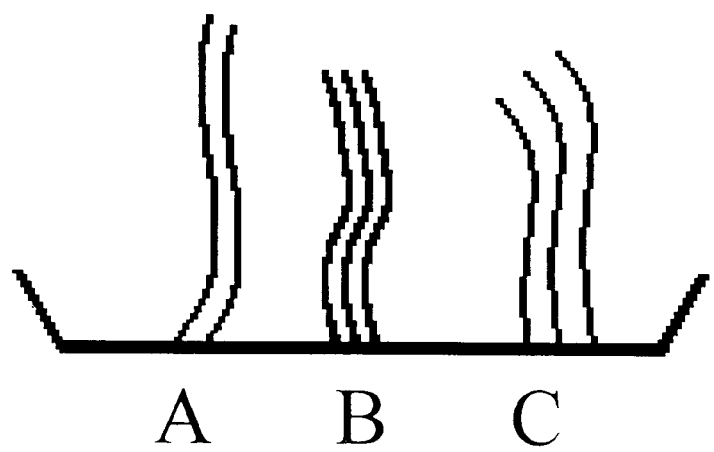
FIG. 7 schematically represents a test region comprising 3 anchors (A, B and C), each of which is present in multiple copies (a "group"). The location of each group of anchors is termed a "locus."
Figure 8:
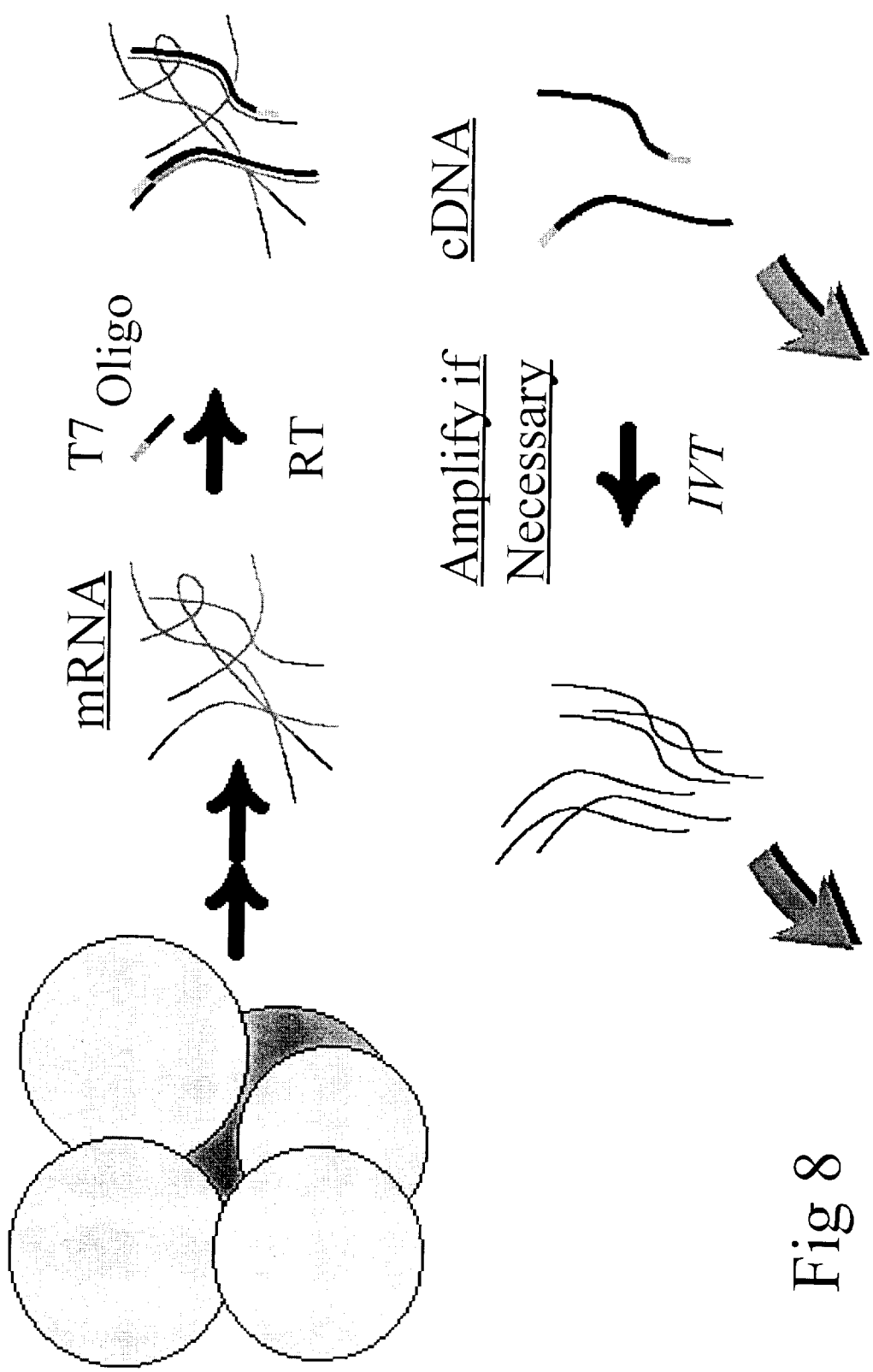
FIG. 8 illustrates an assay in which cDNA(s) generated by specific reverse transcriptase are assayed on MAPS plates.
Figure 9:
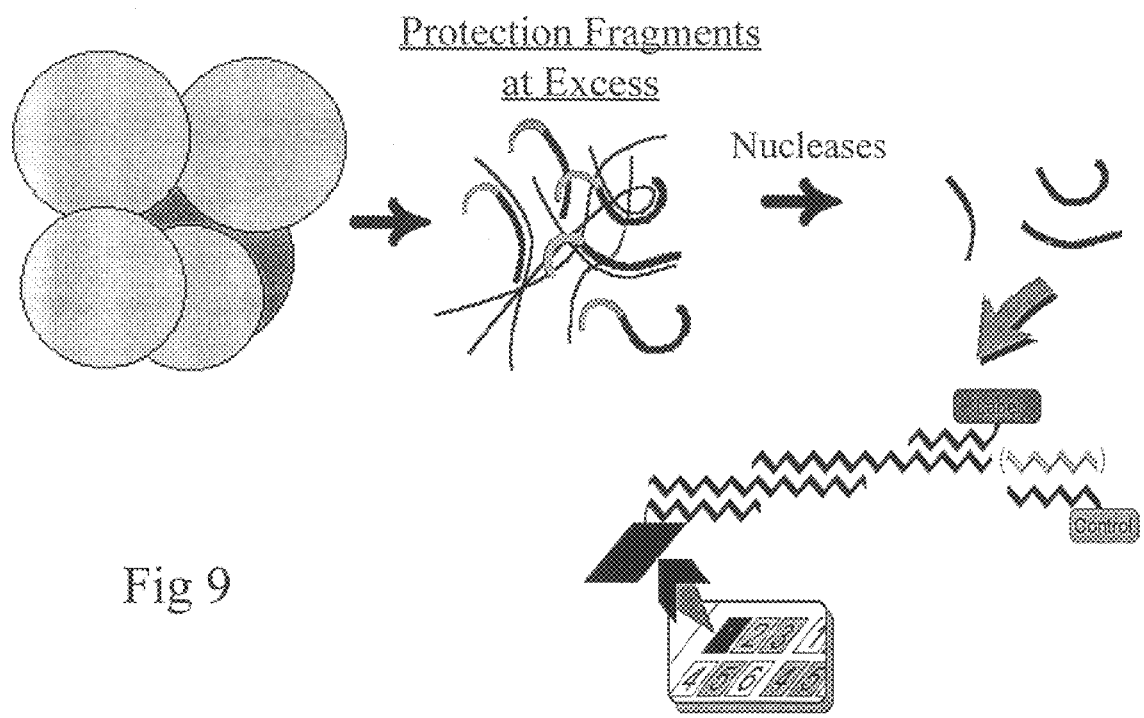
FIG. 9 illustrates an assay which uses a nuclease protection procedure (NPA-MAPS assay). Sample RNA is prepared from cells or from tissue and is represented as thin wavy lines. To the RNA sample is added a group of polynucleotide protection fragments, portrayed as thick, dark and light lines. The dark sections of the protection fragments represent segments that are complementary to specific RNA targets and hybridize to those targets. The light sections represent overhanging portions: sequences contiguous with the complementary sequence but not complementary to target. The protection fragments are added in excess. Following hybridization of all available target to the protection fragments, the samples are treated with an appropriate cocktail of nucleases and with chemical treatments that destroy unwanted non-hybridized RNA and non-hybridized polynucleotide. For example, S1 nuclease can destroy any single stranded DNA present. Hence, excess protection fragment is hydrolyzed as is the overhanging non-hybridized portion of bound protection fragment. RNA can be hydrolyzed by addition of ribonucleases including ribonuclease H and or by heating samples in base. Remaining is a collection of cleaved protection fragments that reflect how much of each target RNA had been present in the sample. The remaining protection fragments are measured by a MAPS hybridization assay.

The rate of hybridization of Cy5-derivatized linker number 1 to its complementary attached anchor is shown, for different concentrations of linker. The generic MAPS plate was prepared as for FIG. 1, except anchor 1 was attached at four spots per well. Incubations were done at room temperature in 5×SSP with 0.1% tween-20, wells were washed 3 times with 5×SSP, and bound fluorescence was measured. A fluorescence picture of the plate was taken with the Tundra, and background was subtracted and the integrated intensity of each spot within each well was calculated with Tundra software. Plotted is the average and standard deviation for the integrated intensity for the four spots within each of two duplicate wells.

Example 3

Fluorescent Linker

A generic MAPS plate is produced with one anchoring oligonucleotide spotted to either 1 spot per well (top two rows), 4 spots per well (next four rows) or 16 spots per well (lower two rows), according to the methods discussed above. To each well complementary, fluorescently labeled, linker is attached by the preferred protocol described in Example 1. Following washing the fluorescence picture of the plate is taken with the Tundra. The amount of fluorescence at each spot reports how much functional linker is available to hybridize to target. The amount of signal detected at repeated spots is highly reproducible.

Example 4

Binding Curves

To the plate prepared as described in Example 3, is added different concentrations of a target oligonucleotide. The linker that has been associated contains a 25-mer sequence complementary to a portion of the target. The target is added in 5×SSC with 0.05% SDS in a total volume of either 30 or 100 microliters, and the plate is covered and incubated at 50° C. overnight. Following hybridization of the target to the attached linker, the target is visualized by a preferred protocol using chemiluminescence. A biotinylated detector oligonucleotide, containing a 25-mer sequence complementary to a separate portion of the target (not to the same portion complementary to linker) is added at 30 nM. Biotinylated detector can be added for 30 minutes after washing away excess unattached target, or it can be added along with target for the length of the overnight hybridization. Following attachment of detector, the surface is washed twice with 5×SSC, once with 1×SSP containing 0.1% Tween-20 and 1% PEG (SSPTP), and a 1:50,000 dilution of 250 ug/ml Horse Radish Peroxidase conjugated to Streptavidin (HRP:SA, from Pierce, Rockford, Ill.) is added for 5 hours in SSPTP at room temperature. Wells are washed four times with SSPTP, and washed once and then incubated with Super Signal Ultra reagent (Pierce). After a few minutes, pictures of luminescence are collected with the Tundra imager, e.g., the picture can accumulate within the CCD array for five minutes. Low levels of target can be visualized in some wells at a target concentration of as little as $\sim 5 \times 10^{-13}$ M; the amount of signal generally becomes saturated at a target concentration of $\sim 10^{-10}$ M. The amount of signal detected at repeated spots is highly reproducible.

Example 5

Figure 12:
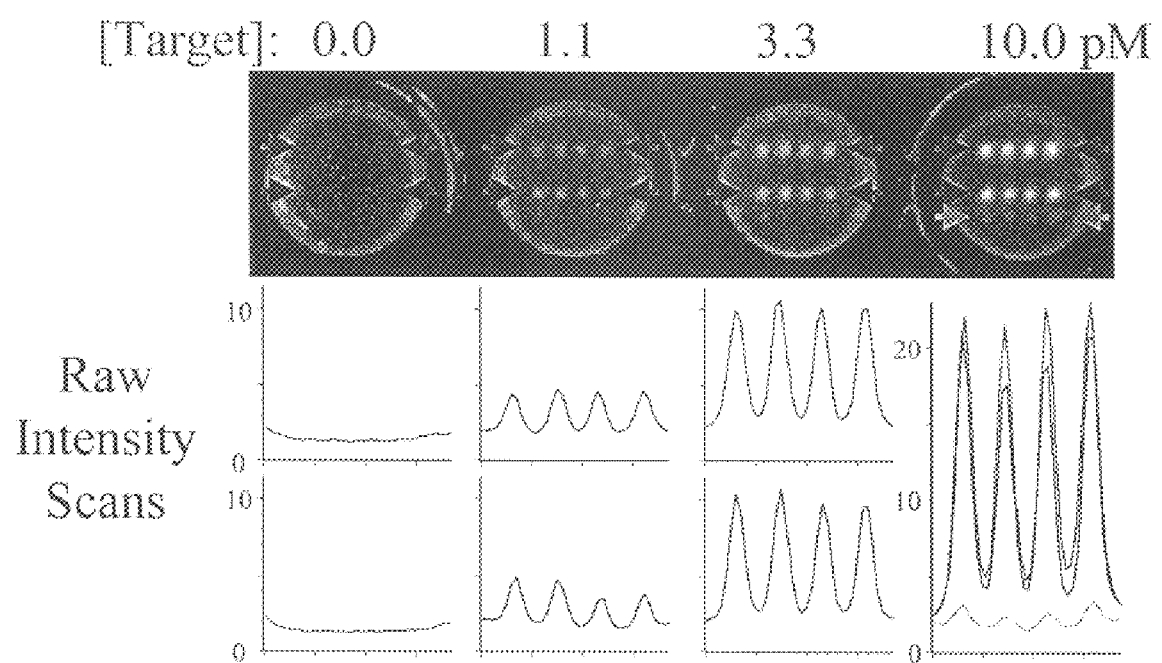
FIG. 12 illustrates a MAPS assay of two oligonucleotide targets.

Assay of Two Oligonucleotides (see FIG. 12)

A binding curve demonstrating a MAPS hybridization assay using the preferred protocol discussed above for two different target oligonucleotides is shown. A generic MAPS plate was prepared with four different anchoring oligonucleotides each spotted four times within each well. For the second and fourth anchor, complementary linker oligonucleotides were self-assembled onto the surface as described. Two targets were added at the concentrations shown in 40 microliters to each well as described, and incubated at 50° C. overnight. The amount of each target attached was visualized by attaching biotinylated detection oligonucleotide specific for each target followed by HRP:SA and chemiluminescence imaging as described. In the lower panel the intensity of the image is quantified. Software that is part of the Tundra Imager package was used to scan the intensity of the images along lines between the arrows shown in the upper panel. At the lowest concentration of target, 1.1 pM, the scanned images show well-defined gaussian peaks at each spot, while there are no discernable background peaks seen in the left-most sample, at 0 concentration of target.

Example 6

Figure 13:
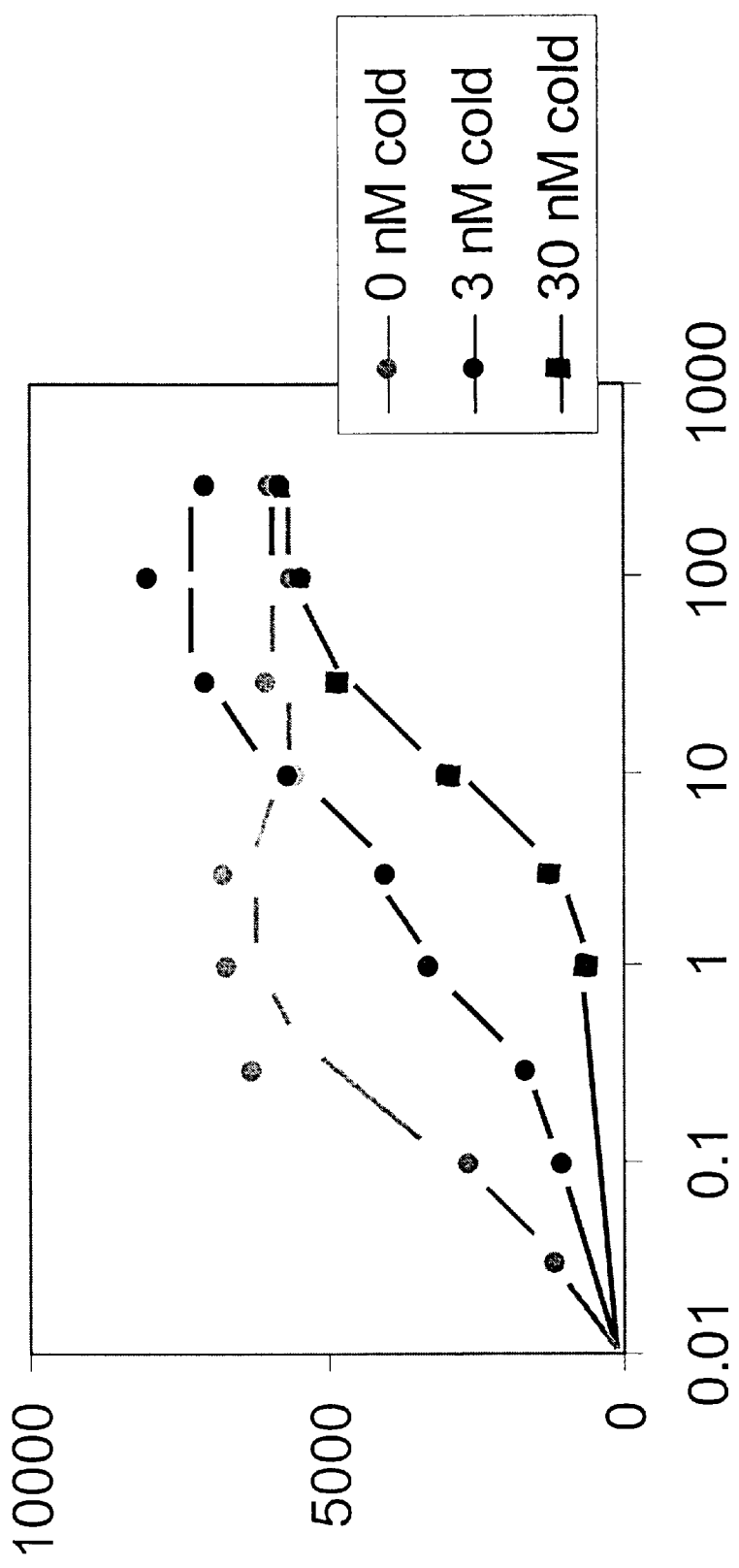
FIG. 13 illustrates the quantification of a sensitivity shift.

Sensitivity Shifting (see FIG. 13)

A MAPS hybridization assay can be used for measuring the concentration of a set of oligonucleotides, by binding them to a surface and labeling them. This works well for those oligonucleotides which are at modest or low concentration. Two samples can be distinguished in such a case because if one sample contains more oligonucleotide, more will bind. On the other hand, if the concentration of targeted oligonucleotide is saturating for the surface (i.e. if it is high enough to occupy all binding sites), then if the concentration goes up no more can bind, so the amount cannot be measured. However, the binding curve of a target can be shifted by adding unlabeled competing ligand.

Binding data are obtained for four different oligonucleotide targets, all of which saturate the surface (i.e. reach maximal binding) at roughly 3 nM. By adding unlabeled competitive targets to all wells, the binding of labeled oligonucleotide is shifted, so that less binds at the lower concentration, and the level at which saturation occurs is moved up. One can add competitive oligonucleotides for, say, targets 1 and 3 but not 2 and 4. This shifts the sensitivity of the assay only for targets 1 and 3. In this way oligonucleotide targets of widely different concentrations can be measured within one assay well, if the relative amount of oligonucleotide expected is known.

The data can be quantified as explained above for the binding of one of the oligonucleotide targets. FIG. 13 shows quantitatively that including competitive oligonucleotide in the assay shifts the binding curve used to assay for this target to higher concentrations.

Figure 14:
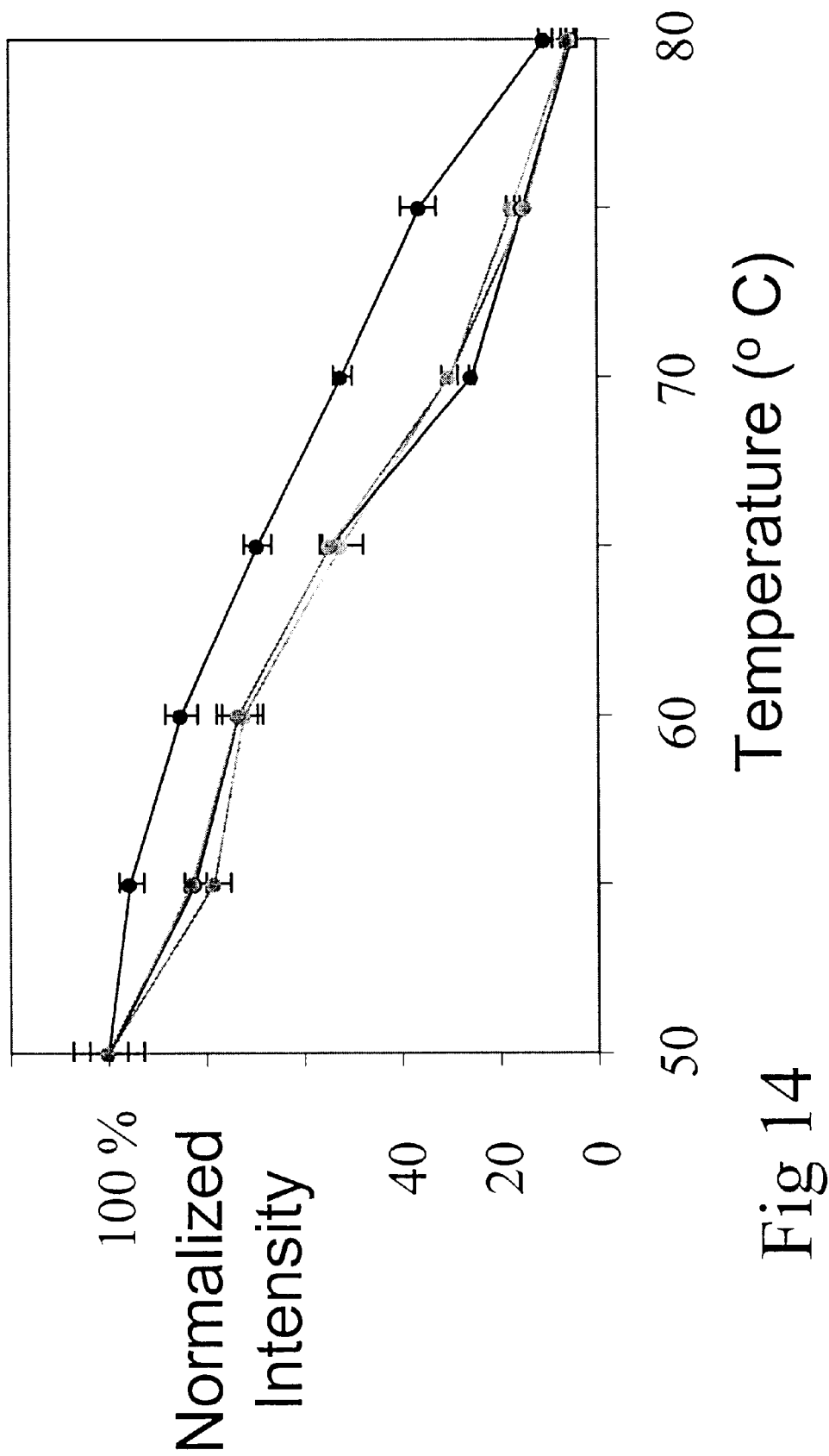
FIG. 14 illustrates melting temperature determinations for four oligonucleotide linker/anchor combinations.

Example 7
Melting Temperature of Four Probes (see FIG. 14)

The amount of four different fluorescent labeled linker oligonucleotides specifically hybridized to anchor oligonucleotides by the MAPS assay is plotted as the temperature is raised. The four oligonucleotides were first allowed to hybridize at 50° C. for 1 hour at 300 nM. Then the wells were washed with SSC without probes, and the amount bound was measured as above by fluorescence (50° C. point). Then the surface was incubated at 55° C. for 30 minutes and the fluorescence bound measured, and so on for all temperatures presented.

Example 8
Detection Methods

Two detection methods can be compared directly. To a MAPS plate with four oligonucleotide anchors attached, each at four spots per well, are added two oligonucleotides to each well, with both including a covalently attached cy5 moiety or both containing a biotin group. The epifluorescence measurement is performed as described for viewing and measurement of the fluorescent linker. The chemiluminescence measurements are performed as described for the MAPS assay using subsequent addition of HRP:SA and a chemiluminescence substrate. The signals generated are roughly of the same magnitude. However, for the geometry of the microplates, which contain walls separating each well, and occasional bubbles of liquid or a miniscus of fluid, reflections in the epi-fluorescence images can cause interference in data interpretation.

Example 9
Chemiluminescence Products

Two products available as chemiluminescence substrates for horse radish peroxidase can be compared as detection procedures for the MAPS assay. A MAPS plate is prepared as for Example 8, and incubated with biotinylated linker oligonucleotides. Then either alkaline phosphatase coupled to streptavidin (AlkPhos:SA) or HRP:SA is added, followed by washing and addition of either CDP-Star (Tropix) to the wells with AlkPhos:SA or ECL-Plus to the wells with HRP:SA. Labeling with SA derivatized enzymes and substrates is as suggested by the manufacturers for use in labeling of western blots. These two (as well as other available substrates) can both be used to assess oligonucleotide hybridization to MAPS plates.

Example 10
Resolution at 0.6 mm

The resolution of the current system for MAPS assay is tested by preparing a MAPS plate with four different oligonucleotide anchors per well each spotted four times per well, with a pitch (center-to-center spacing) of 0.6 mm. Then either cy5-derivatized linkers or biotinylated linkers are hybridized and detected and scanned as above. For the epi-fluorescence measurement the resolution is higher (and pitch could likely be reduced). For the chemiluminescence detection procedure neighboring spots are not completely separated, yet at this spacing individual peaks may be resolved unambiguously by computer deconvolution.

Example 11
Test Nuclease Protection Protocol

In an assay to test for the optimal conditions for hybridization and nuclease treatment for the nuclease protection protocol, the Nuclease Protection Assay kit from Ambion (Austin, Tex.) is used to provide conditions, buffers and enzymes. Eight samples are prepared in one of three buffers. Hyb Buff 1 is 100% Hybridization Buffer (Ambion); Hyb Buff 2 is 75% Hybridization Buffer and 25% Hybridization Dilution Buffer (Ambion); and Hyb Buff 3 is 50% of each. A 70-mer oligonucleotide that contains 60 residues complementary to a test mRNA is synthesized (Biosource International, Camarillo, Calif.) and labeled with Psoralen-fluorescein (Schleicher and Schuell, Keene, N.H.) following the protocol as suggested for labeling of Psoralen-biotin by Ambion. Briefly, protection fragment is diluted to 50 ug/ml in 20 μls of TE buffer(10 mM Tris, 1 mM EDTA, pH 8) boiled for 10 minutes, and rapidly cooled in ice water. Four μls of 130 ug/ml Psoralen-fluorescein in DMF is added, and the sample is illuminated for 45 minutes at 40° C. with a hand-held long wavelength UV source. Free Psoralen-fluorescein is removed by extraction with saturated butanol. The mRNA used is GAPDH anti-sense mRNA, prepared from antisense plasmid (pTRI-GAPDH-Mouse antisense Control Template from Ambion) using T7 promoter and the MaxiScript kit (Ambion). The short protection fragment is the 60-mer complementary portion synthesized separately and similarly labeled. The sequences of the protection fragments are as follows:

```
Full length protection fragment:                                     SEQ ID:23
CGAGAAATATGACAACTCACTCAAGATTGTCAGCAATGCATCCTGCACCACCAACTGCTTGCT
TGTCTAA Short protection fragment:                                           SEQ ID:24
CGAGAAATATGACAACTCACTCAAGATFGTCAGCAATGCATCCTGCACCACCAACTGCTT
```

Hybridizations are done by mixing protection fragments at 20 nM and GAPDH mRNA at 60 nM in 10 μls final volume for two hours at 22° C. or 37° C. Following hybridization, 200 μls of a mixture of nucleases is added according to instructions from the manufacturer (Ambion Nuclease Protection Kit, 1:200 dilution of nuclease mixture) and incubated again at the same temperatures for 30 minutes. Hydrolysis is stopped with Hybridization Inhibition Buffer (Ambion), and oligonucleotides are pelleted and washed with Ethanol. 10 μls of 1×Gel Loading Buffer (Ambion) is added and oligonucleotides are separated on a 15% TBE-urea gel. The gel is swirled in running buffer for 30 minutes, put on a plastic plate and imaged with the Tundra using fluorescein filters for selecting excitation and emission wavelengths. The image is accumulated on the CCD array for 2 minutes. Best conditions are those for samples incubated in Hyb Buff 2 at 37° C. or in Hyb Buff 3 at 22° C. In these samples no detectable full-length protection fragment remains, and significant amounts of a portion of the full-length protection fragment at a size apparently the same as the short protection fragment are seen.

Example 12
mRNA Assay by NPA-MAPS. (see FIG. 15)

The full NPA-MAPS protocol was used, with conditions for hybridization and nuclease treatment similar to those described in Example 1. Ten samples were run for the assay. All contained the same amount of the 70-mer oligonucleotide protection fragment and different amounts of GAPDH mRNA. Hybridization samples in 10 μls in 50% Hybridization Buffer and 50% Dilution Buffer containing 0.08 mg/ml Yeast RNA (Ambion) were heated to 90° C. for 6 minutes, briefly centrifuged, heated to 70° C. for 5 minutes, and allowed to cool to 19° C. and incubated for 19 hours. 200 μls of nuclease mixture was then added to each sample for 30 minutes at 19° C. 60 μls was aliquoted from each sample for the MAPS assay. 2 μls of 10 N NaOH and 2 μl of 0.5 M EDTA was added, and the sample heated to 90° C. for 15 minutes, 37° C. for 15 minutes, and allowed to sit at room temperature for 20 minutes. Then samples were neutralized with 2 μl of 10 M HCl, and 12 μls of 20×SSC containing 2 M HEPES pH 7.5 and 200 nM biotinylated detector oligonucleotide specific for the protection fragment was added along with 1 μl of 10% SDS. Samples were mixed, heated to 80° C. for 5 minutes, and two 35 μl aliquots of each sample were pipetted to two wells of a MAPS plate (each sample was split in two and run in duplicate on the MAPS plate). The plate had been prepared as for standard MAPS protocol, with self-assembled CY5-derivatized linker specific for the protection fragment already attached. The MAPS plate was covered and incubated at 50° C. overnight, and detection and luminescence performed as described. In the last sample, no nucleases were added during the assay as a control to visualize how the protection fragment alone would be detected by MAPS. In the lower portion of the figure, the intensity scan (as analyzed by the imager) for the top row of wells is presented. The amount of GAPDH mRNA present in the sample (that is, the amount in each duplicate well after aliquoting to the MAPS plate) is listed in the figure.

The oligonucleotides used for the MAPS plates were as follows:

duplicate wells are plotted for each concentration of mRNA. A binding curve is superimposed, of the form:

$$\text{Fraction Bound} = \text{Max Bound} * 1/(1+IC_{50}/L)$$

where Max Bound is the maximum bound at saturation, Fraction Bound is the amount bound at ligand concentration, L, and the $IC_{50}$ is the concentration of ligand at which the Fraction Bound is half of Max Bound. The curve is shown as red dots on the figure, drawn with a best fit value of $IC_{50}=4.2$ femtomoles as labeled in the figure.

Example 14
NPA-MAPS Assay of GAPDH mRNA in a Total Mouse Liver RNA Extract

A total mouse RNA extract is assayed for GAPDH mRNA with an NPA-MAPS assay and a dilution curve is made. Total RNA from mouse liver is prepared using a Qiagen kit. RNA is precipitated in 70% EtOH with 0.5 M Mg-Acetate, and resuspended in 10 μls of 5×SSC with 0.05% SDS with 1.8 nM protection fragment. The protection fragment added is an oligonucleotide 70 bases long, 60 bases of which are complementary to mouse GAPDH. Either a fragment complementary to mouse GAPDH mRNA is used ("protection fragment"), or the complement of the sequence is used as a negative control ("antisense fragment").

RNA samples with protection fragments are heated to 90° C. for 5 minutes, and hybridizations are done by bringing samples to 70° C. and allowing them to cool slowly to room temperature over night. S1 nuclease (Promega) at 1:10 dilution is added in 30 μls of 1×S1 Nuclease Buffer (Promega) for 30 minutes at 19° C., and stopped by 1.6 μls of 10 N NaOH and 2.7 μls of 0.5 M EDTA. Samples are heated to 90° C. for 15 minutes and then 37° C. for 15 minutes to denature and destroy RNA, neutralized with 1.6 μls of 10 M HCl, and incubated on MAPS plates overnight in 5×SSC with 0.05% SDS supplemented with 200 mM HEPES pH 7.5 to which 30 nM biotinylated detection oligonucleotide is added. Washing and visualization with SA-HRP is done as described. The amount of signal decreases in parallel with decreasing amounts of mouse RNA (samples include 500, 170, 50, 5, or 0.5 μg of total mouse RNA. Two control samples are included to which no

```
Anchor*:                                                                      SEQ ID:25
    CGCCGGTCGAGCGTTGTGGGAGCGC
Linker**                                                                      SEQ ID:26
    CTTGAGTGAGTTGTCATATTTCTCGGATACTGAGTGCGCTCCCACAACGCTCGACCGG
    CG
Protection fragment (complementary to mouse antisense mRNA for GAPDH)
                                                                              SEQ ID:27
    CGAGAAATATGACAACTCACTCAAGATTGTCAGCAATGCATCCTGCACCACCAACTGC
    TTGCTTGTCTAA
Detector Oligonucleotide***-labeled at 5' end with biotin                     SEQ ID:28
    AAGCAGTTGGTGGTGCAGGATGCAT
```

*Anchors were synthesized with C12 spacer with amide at the 5' end
**Linkers were synthesized with Cy5 attached at the 5' end
***Detector Oligonucleotides were synthesized with biotin attached at the 5' end

Example 13

Figure 16:
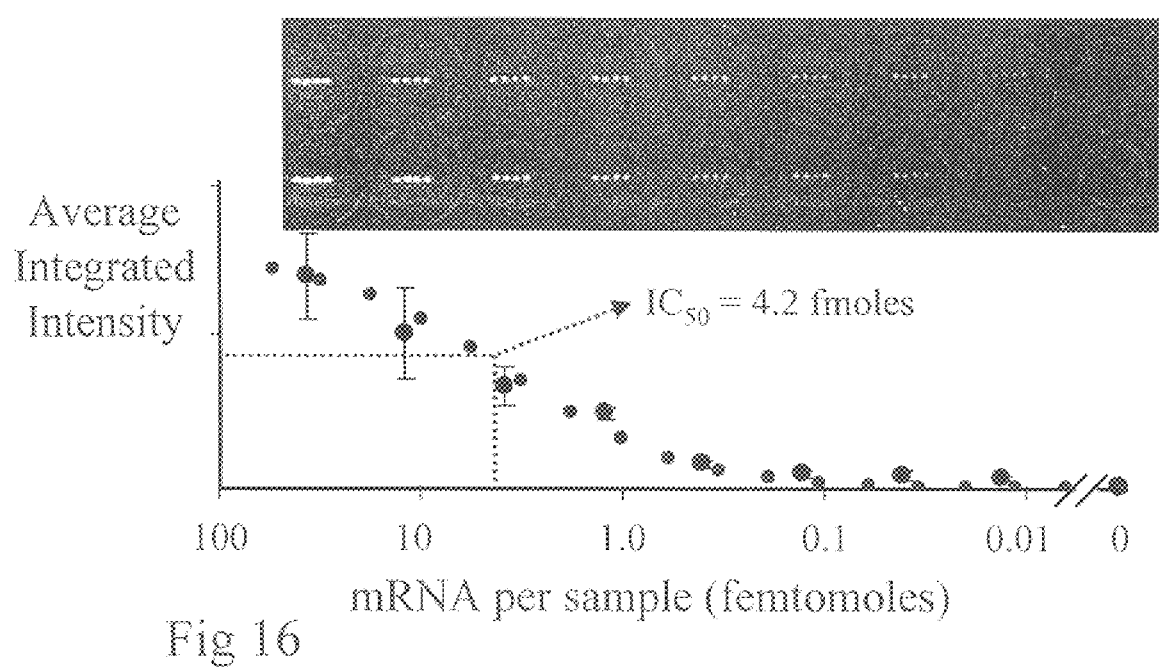
FIG. 16 illustrates a dilution curve with NPA-MAPS.

Dilution Curve, NPA-MAPS (see FIG. 16)

Figure 15:
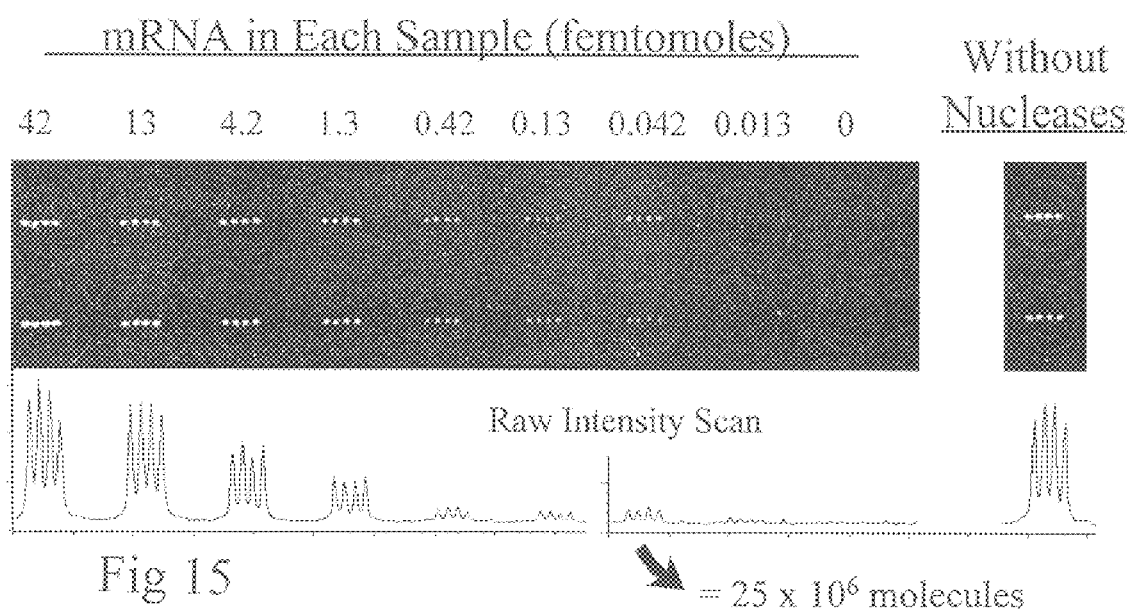
FIG. 15 illustrates an mRNA assay by NPA-MAPS.

The data discussed in Example 12 and shown in FIG. 15 were quantified and plotted as a dilution curve. The average and standard deviations for all eight spots of the two S1 nuclease is added. Signal is seen only for the complementary protection fragment.

Oligonucleotides used:

For Antisense Control (same oligonucleotides as for example 12):

```
Anchor*:                                                                SEQ ID:25
    CGCCGGTCGAGCGTTGTGGGAGCGC
Linker**                                                                SEQ ID:26
    CTTGAGTGAGTTGTCATATTTCTCGGATACTGAGTGCGCTCCCACAACGCTCGACCGG
    CG
Protection fragment (complementary to mouse antisense mRNA for GAPDH)   SEQ ID:27
    CGAGAAATATGACAACTCACTCAAGATTGTCAGCAATGCATCCTGCACCACCAACTGC
    TTGCTTGTCTAA
    Detector Oligonucleotide***                                         SEQ ID:28
        AAGCAGTTGGTGGTGCAGGATGCAT For Sense GAPDH mRNA samples:
    Anchor*:                                                            SEQ ID:25
        CGCCGGTCGAGCGTTGTGGGAGCGC
    Linker**                                                            SEQ ID:29
        ATGCATCCTGCACCACCAACTGCTTGATACTGAGTGCGCTCCCACAACGCTCGACCGGCG
    Protection fragment (complementary to mouse mRNA for GAPDH):        SEQ ID:30
        AAGCAGTTGGTGGTGCAGGATGCATTGCTGACAATCTTGAGTGAGTTGTCATATTTCT
        CGGCTTGTCTAA
    Detector Oligonucleotide***                                         SEQ ID:31
        CGAGAAATATGACAACTCACTCAAG

*Anchors were synthesized with C12 spacer with amide at the 5' end
**Linkers were synthesized with Cy5 attached at the 5' end
**Probes were synthesized with biotin attached at the 5' end
```

Example 15
A Nuclease Protection MAPS Assay with Controls mRNA is extracted from mouse liver and nuclease protection is performed essentially as described in Example 14, except that the GADPH specific protection fragment comprises 60 nucleotides which are complementary to mouse GAPDH, followed by 15 "overhanging" nucleotides at the 3' end of the fragment which are not complementary to the target. After hybridization and nuclcase digestion the remaining protection fragment is hybridized to a MAPS plate as indicated in Example 14, except that two different oligonucleotide detection fragments are used to detect the immobilized protection fragment. One detection fragment is complementary to the GAPDH-specific portion of the protection fragment, and the other, a control, is complementary to the 15 base overhang portion of the protection fragment. Each detection fragment is used on different replicate samples (i.e., in different wells), so that both detection fragments can be labeled with the same detection molecule. In the present example both fragments are labeled with HRP. Without the addition of nuclease, signals from both of the detection fragments are seen; whereas, when nuclease digestion is performed only the signal corresponding to the GAPDH sequences can be detected. The amount of GAPDH-specific signal is reduced relative to that observed in the absence of nuclease digestion, because the protection fragment is added at excess relative to the amount of GAPDH mRNA present. This allows the amount of GAPDH mRNA to be limiting to the protective hybridization, so that the amount of double-stranded hybrid formed (and therefore the amount of protection fragment that is protected from the nuclease) reflects the amount of mRNA. When no mRNA is included in the reaction mixture, neither signal can be detected when nucleases are added. The above findings demonstrate that the hybridization and digestion steps of the assay occurred as desired.

When protection fragments corresponding to a variety of targets are included in a given assay, each of the protection fragments can comprise the same 15 base overhang portion. This allows for one detection fragment to be used to test for remaining overhang for all samples.

Example 16
A Transcription Assay Screening for Compounds that may Alter the Expression of Genes that are Correlative with a Disease State A cell line derived from a human tumor is used. It is found to express 30 genes at higher levels than do normal cells. (That is, these 30 genes are being used more than in normal cells, to make mRNA and then to make the protein for which the genes are the instructions. A transcription assay measures how much the genes are being used by measuring how much mRNA for each gene is present.) Using a nuclease protection assay on MAPS plates (NPA-MAPS), 8800 chemical compounds are tested to see if growing the cells in the presence of the compounds can reduce the expression of some of the 30 correlative genes without affecting the expression of six normal (constitutive, "housekeeping") genes. Any compounds having that effect might be useful in the future development of drugs for treating this kind of tumor.

About 10,000 to 100,000 cells are added to each well of 100 96-well polystyrene plates and the cells are grown for 2 days until they cover the surface of each well. For 8 wells of each plate, the cells are left to grow without additions. To the remaining 88 wells of each plate, a different chemical compound is added so that the effect of it alone can be tested. For the 100 plates used at one time, 8800 compounds can be tested or screened. The cells are grown for 24 hours in the presence of the compounds, and then the cells are harvested for assay. The cells in each plate are treated according to the instructions for preparing RNA in samples from 96-well plates (for example according to the Qiagen RNeasy 96 kit). After the RNA is prepared, the amount of each of 36 different mRNA species is quantified by the NPA-MAPS approach, including the 30 correlative genes and 6 normal "housekeeping" genes. 36 DNA oligonucleotide protection fragments, each corresponding to one of the genes of interest, are added to each well and allowed to hybridize under selected stringent conditions to their target mRNA sequences. Then S1 nuclease is added to destroy excess unhybridized DNA, and the samples are treated chemically to destroy the RNA as well. Left is the oligonucleotide protection fragment for each of the 36 genes in proportion to how much mRNA had been present in the treated cells for each sample.

One hundred 96-well plates, each of which comprises an array of a plurality of 36 different anchor oligonucleotides in each well, are prepared by adding to each well 36 different linker oligonucleotides. The linkers self-assemble on the surface of each well, converting the generic plates to MAPS plates comprising specific probes for each of the 36 oligonucleotide protection fragments. Each linker has a portion specific for one of the 36 anchors and a portion specific for a segment of one of the 36 protection oligonucleotides. The oligonucleotide sample from each well of the 100 sample plates is added to a corresponding well of the 100 MAPS plates. After hybridization under selected stringent conditions, a detection oligonucleotide for each target with a chemiluminescent enzyme attached is added, so that each specific spot of each well lights up in proportion to how much mRNA had been present in the sample. Any wells that show reduced amounts of correlative genes with no effect on the 6 house keeping genes are interesting. The compounds added to the cells for those samples are possible starting points to develop anti-tumor agents.

Example 17

Induced and Constitutive Gene Expression

RNA was prepared essentially as described in Example 14, from the livers of mice either not infected ("Control") or one hour after infection ("Infected") by adenovirus. 60 µgs of liver RNA was used for each sample, and samples were prepared in duplicate. Each assay well contained three sets of duplicate loci, corresponding to the three genes described above. Each locus contained an anchor, bound to a linker comprising a probe which was complementary to a protection fragment corresponding to one of the three genes. A nuclease protection MAPS assay was performed essentially as described in FIG. 12, and the images were collected and scanned as described. Shown are the raw image data collected and the intensity scans for duplicate wells for each of the three mRNA targets. The numbers over the scan lines are the integrated intensity values and standard deviations for each condition (n=4). The house-keeping gene, GAPDH, not expected to change, showed a modest increase of 1.3-fold in the infected sample that was not statistically significant. The transcription of MIP-2 and c-jun was increased 4 and 6-fold, respectively. These findings demonstrate that two genes, MIP-2 and c-jun, exhibit enhanced expression in response to adenovirus infection, compared to a control, constitutively expressed gene—GAPDH.

Example 18

Figure 17:
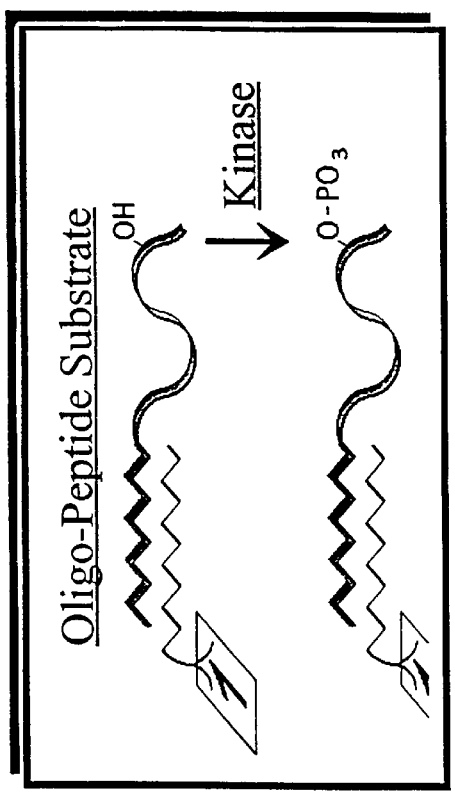
FIG. 17 illustrates an assay to detect peptides containing phosphotyrosine residues.
Figure 17:
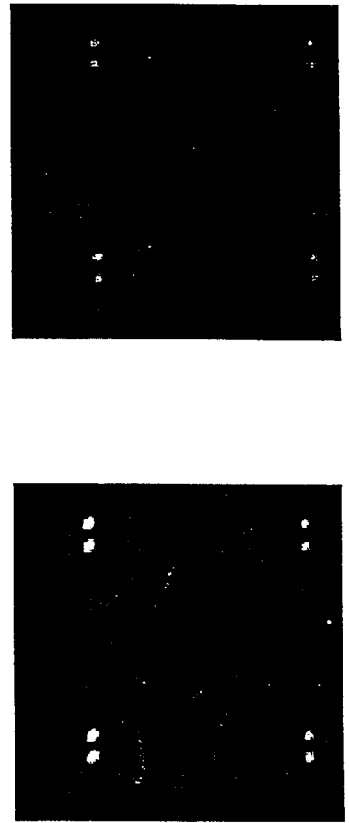

An Enzyme Assay Screening for Compounds that Selectively Inhibit Tyrosine or Serine Kinases (see FIG. 17)

Kinases are enzymes that attach a phosphate to proteins. Many have been shown to stimulate normal and neoplastic cell growth. Hence, compounds that inhibit specific kinases (but not all kinases) can be used to test whether the kinases are involved in pathology and, if so, to serve as starting points for pharmaceutical development. For example, five tyrosine kinases that are involved in stimulating cell growth or in regulating the inflammatory response are src, 1ck, fyn, Zap70, and yes. Each kinase has substrates that are partially identified, as short peptides that contain a tyrosine. Some of the kinase specificities overlap so that different kinases may phosphorylate some peptides equally but others preferentially. For the five kinases, 36 peptide substrates are selected that show a spectrum of specific and overlapping specificities.

One hundred 96-well plates are used; each well comprises 36 generic oligonucleotide anchors. 36 linkers are prepared to convert the generic oligonucleotide array (with anchors only) to arrays comprising peptide substrates. The 36 peptide substrates are synthesized and each is attached covalently through an amide bond, for example, to an oligonucleotide containing a 5' amino group. The oligonucleotides contain sequences that hybridize specifically to the anchors. The peptide/oligo linkers are self assembled on the surface by adding them to all wells of the MAPS plates.

For screening, the five kinases at appropriate concentrations (so that the rates of phosphorylation of the substrates are balanced as much as possible) are added to each well along with one of 8800 different compounds to be tested. The compounds are tested for their ability to directly inhibit the isolated enzymes. The amount of phosphorylation of each arrayed peptide is detected by adding labeled antibodies that bind only to peptides that are phosphorylated on tyrosine. Any wells that show a reduction in some of the phospho-tyrosine spots but not all of the spots are interesting. Compounds that had been added to those wells can be tested further as possible selective inhibitors of some of the kinases tested.

The scheme of the assay is shown in the top panel of FIG. 17. A chimeric linker molecule is prepared in which a 25 base pair oligonucleotide complementary to one of the anchors is crosslinked to a peptide substrate of a tyrosine phosphokinase enzyme. The chimeric oligo-peptide substrate self-assembles onto an array of oligonucleotide anchors, the kinase enzyme is used to phosphorylate the peptide portion of the chimera, and after the enzyme reaction is allowed to proceed, the amount of phosphorylation of the peptide is determined by anti-phoshotyrosine or anti-phosphoserine antibodies with an attached detection fluorophore or enzyme.

The results of the assay are shown in the lower panel. The homobifunctional crosslinker, DSS (Pierce), was used to attach the 5' amino group of an oligonucleotide linker to the N terminus of a peptide synthesized with a phosphorylated tyrosine. The sequence of the peptide in single-letter code was: TSEPQpYQPGENL (SEQ ID: 32), where pY represents phosphotyrosine. The chimera was either used directly or first brought to pH 14 for 60 minutes in order to partially hydrolyze the phosphate group from the tyrosine. The phosphorylated or partially dephosphorylated chimeric molecules were self-assembled onto complementary anchor molecules within a MAPS plate at the concentrations shown for one hour. After washing and blocking the wells with 0.3% BSA in SSPTP antiphosphotyrosine antibody crosslinked to HRP (antibody 4G10 from Upstate Biotechnology, Lake Placid, N.Y.) was added at a 1:3000 dilution in SSPTP for one hour, and the amount of antibody attached detected with chemiluminescence substrate, Super Signal Blaze. The image shown was accumulated on the CCD array for 1 minute. As expected a difference was seen in the amount of phosphate attached to the oligo-peptide. This difference is the basis for an assay measuring how active a series of kinases is when treated with different possible inhibitors.

Example 19

A Binding Assay for the Detection of Selective Inhibitors of the Interaction Between SH2 Domains and Phosphorylated Peptides SH2 domains serve as docking subunits of some growth regulatory proteins. The domains bind to phosphotyrosine containing proteins or peptides with imperfect specificity. That is, some phosphotyrosine peptides bind specifically to one or to few SH2 proteins while others bind widely to many SH2 proteins.

For this assay, the linkers are phosphorylated peptides covalently attached to oligonucleotides. The peptide moieties are selected for their ability to bind to a group of selected SH2 proteins. The linkers convert generic MAPS plates to plates with ligands specific for the group of SH2 proteins. 100 96-well MAPS plates bearing the ligands are generated. The proteins are isolated and labeled with, for example, a cy5 fluorescent molecule.

In order to screen for inhibitors of the SH2 domain/ phosphopeptide interaction, the group of labeled SH2 proteins is added to each well of the 100 96-well MAPS plates, and in each well a different test compound is added. Hence the effect of each compound individually on the interaction of the SH2 proteins with their phosphopeptide ligands is tested. The assay is to measure the fluorescence of bound SH2 protein associated with each surface-bound peptide linker. For any well showing reduced fluorescence at some spots but not all spots, the compound added can be further tested as a putative selective inhibitor of SH2 docking.

Example 20

High Throughput Screening (see FIG. 22)

Shown is a high throughput MAPS plate demonstrating the detection of signal from 96 wells in a single experiment. Hybridization to the same oligonucleotide was measured with 16 replicates in 80 wells. As shown, the reproducibility of the 1280 hybridization assays was very high. The leftmost and right-most columns served as controls to standardize the signal for different concentrations of the oligonucleotide.

In a similar fashion, 16 different oligonucleotides can be tested in each well, and the test repeated in the 80 different wells of the plate. Of course, an even greater number of different oligonucleotides or other probes, (e.g., 100 nucleotide probes) can be assayed in each well, and many plates can be tested simultaneously (e.g., 100 plates, such as 96-well microtiter plates). The large number of assays which can be performed on each sample (e.g., in the latter case, about 100 different assays) and the large number of samples which can be assayed simultaneously (e.g., in the latter case, about 96×100, or 9600 different samples) provides for very high throughput.

From the foregoing description, one skilled in the art can easily ascertain the essential characteristics of this invention, and without departing from the spirit and scope thereof, can make changes and modifications of the invention to adapt it to various usage and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above and in the figures are hereby incorporated by reference.

What is claimed is:

1. A method of determining which of a plurality of ESTs are complementary to a given nucleic acid, comprising,
   a) incubating an immobilized array of oligonucleotide probes, wherein at least one of said probes is complementary to a portion of a first strand of each of said plurality of ESTs, and wherein the second strands of at least two of said ESTs are complementary to different or overlapping portions of said given nucleic acid, with a test sample which may contain said given nucleic acid, to obtain, if said test sample contains said given nucleic acid, hybridization products between said oligonucleotide probes and said given nucleic acid,
   b) incubating the hybridization products in said array with a detector oligonucleotide, wherein, for each hybridization product, said detector oligonucleotide is complementary to a portion of a first strand of an EST to which the oligonucleotide probe in said hybridization product is complementary, but which is complementary to a different portion of that EST strand than is said oligonucleotide probe, and
   c) detecting which oligonucleotide probes of said array are labeled by said detector oligonucleotide, thereby determining which of said plurality of ESTs are complementary to said given nucleic acid,
      wherein said array of oligonucleotide probes is immobilized on a region of a combination, wherein said combination comprises
         i) a surface comprising a number of spatially discrete, substantially identical, regions equal to the number of ESTs to be studied, each region comprising
         ii) a number of different anchors equal to the number of ESTs to be studied, each anchor in association with
         iii) a bifunctional linker which has a first portion that is specific for the anchor, and a second portion that comprises an oligonucleotide probe which is specific for at least one of said ESTs.

2. The method of claim 1, further comprising, after a) and/or b), removing unbound portions of said sample.

3. The method of claim 1, which is a method of determining which of at least eight ESTs are complementary to a given nucleic acid.

4. The method of claim 3, comprising
   a) contacting each of a number of samples corresponding to the number of ESTs to be studied, wherein each of said samples may comprise molecules of said given nucleic acids, with a different region of a combination, wherein each said region comprises an array of oligonucleotide probes, at least one of which is complementary to a portion of a first strand of each of said ESTs,
   b) incubating said samples with said regions, thereby permitting molecules of said nucleic acid to bind to said oligonucleotide probes, thereby forming hybridization products, and
   c) incubating each of said regions comprising said hybridization products with a different detector oligonucleotide, wherein each of said detector oligonucleotide is complementary to a portion of a first strand of an EST to which a given one of the oligonucleotide probes of said array corresponds, but which is complementary to a different portion of the EST strand than is said given oligonucleotide probe, thereby binding detector oligonucleotides to nucleic acid molecules which have bound to said given oligonucleotide probe or to other oligonucleotide probes which are complementary to said nucleic acid.

5. A method of determining which of a plurality of ESTs are complmentary to a given nucleic acid, comprising, a) incubating a collection of bifunctional oligonucleotide linker molecules, each of which comprises a first portion which is an oligonucleotide probe that is complementary to a portion of a first strand of at least one of said plurality of ESTs, and a second portion which is specific for an anchor oligonucleotide, with a test sample which may contain said given nucleic acid, to obtain, if said test sample contains said given nucleic acid, a first set of hybridization products between said oligonucleotide probes and said given nucleic acid, wherein the second strand of at least two of said ESTs are complementary to different or overlapping portions of said given nucleic acid, b) incubating said first hybridization products with an immobilized array of anchor oligonucleotides, wherein each anchor oligonucleotide is complementary to the anchor-specific portion of at least one of said linker molecules, to form a second set of hybridization products comprising said anchors, said linker molecules and said given nucleic acid, and c) incubating either said first or said second hybridization product with a detector oligonucleotide, wherein, for each hybridization product, said detector oligonucleotide is complementary to a portion of a first strand of an EST to which the oligonucleotide probe in said hybridization product is complementary, but which is complementary to a different portion of that EST strand than is said oligonucleotide probe, and d) detecting which oligonucleotide probes of said array are labeled by said detector oligonucleotide,
wherein said array of anchor oligonucleotide is immobilized on a region of a combination, wherein said combination comprises
i) a surface comprising a number of spatially discrete, substantially identical, regions equal to the number of ESTs to be studied, each region comprising
ii) a number of different anchors equal to the number of ESTs to be studied.

6. The method of claim 5, further comprising, after a), b) and/or c), removing unbound portions of said sample.

7. The method of claim 5, which is a method of determining which of at least eight ESTs are complementary to a given nucleic acid.

8. A method of determining which of a plurality of polynucleotides are complementary to a given nucleic acid, comprising, a) incubating an immobilized array of oligonucleotide probes, wherein at least one of said probe is complementary to a portion of a first strand of each of said plurality of polynucleotides, and wherein the second strands of at least two of said polynucleotides are complementary to different or overlapping portions of said given nucleic acid, with a test sample which may contain said given nucleic acid, to obtain, if said test sample contains said given nucleic acid, hybridization products between said oligonucleotide probes and said given nucleic acid, b) incubating the hybridization prodcts in said array with a detector oligonucleotide, wherein, for each hybridization product, said detector oligononucleotide is complementary to a portion of a first strand of a polynucleotide to which the oligonucleotide probe in said hybridization product is complementary, but which is complementary to a different portion of that polynucleotide strand than is said oligonucleotide probe, and c) detecting which oligonucleotide probes of said array are labeled by said detector oligonucleotide, thereby determining which of said plurality of polynucleotides are complementary to said given nucleic acid,
wherein said array of oligonucleotide probes is immobilized on a region of a combination, wherein said combination comprises
i) a surface comprising a number of spatially discrete, identical, regions equal to the number of polynucleotides to be studies, each region comprising
ii) a number of different anchors equal to the number of polynucleotides to be studied, each anchor in association with
iii) a bifunctional linker which has a first portion that specific for the anchor, and a second portion that comprises an oligonucleotide probe which is specific for at least one of said polynucleotide.

9. The method of claim 8, further comprising, after a), b) and/or c), removing unbound portions of said sample.

10. The method of claim 8, which is a method of determining which of at least eight polynucleotides are complementary to a given nucleic acid.

11. The method of claim 10, comprising a) contacting each of a number of samples corresponding to the number of polynucleotides to be studied, wherein each of said samples may comprise molecules of said given nucleic acid, with a different region of a combination, wherein each said region comprises an array of oligonucleotide probes, at least one of which is complementary to a portion of a first strand of each of said polynucleotides, b) incubating said samples with said regions, thereby permitting molecules of said nucleic acid to bind to said oligonucleotide probes, thereby forming hybridization products, and c) incubating each of said regions comprising said hybridization products with a different detector oligonucleotide, wherein each of said detector oligonucleotides is complementary to a portion of a first strand of an polynucleotide to which a given one of the oligonucleotide probes of said array corresponds, but which is complementary to a different portion of the polynucleotide strand than is said given oligonucleotide probe, therby binding detector oligonucleotides to nucleic acid molecules which have bound to said given oligonucleotide probe or to other oligonucleotide probes which are complementary to said nucleic acid.

12. A method of determining which of a plurality of ESTs are complementary to a given nucleic acid, comprising;

a) incubating an immobilized array of oligonucleotide probes, wherein at least one of said probes is complementary to a portion of a first strand of each of said plurality of ESTs, and wherein the second strands of at least two of said ESTs are complementary to different or overlapping portions of said given nucleic acid, with a test sample which may contain said given nucleic acid, to obtain, if said test sample contains said given nucleic acid, hybridization products between said oligonucleotide probes and said given nucleic acid, b) incubating the hybridization products in said array with a detector oligonucleotide, wherein, for each hybridization product, said detector oligonucleotide is complementary to a portion of a first strand of an EST to which the oligonucleotide probe in said hybridization product is complementary, but which is complementary to a different portion of that EST strand than is said oligonucleotide probe, and c) detecting which oligonucleotide probes of said array are labeled by said detector oligonucleotide, thereby determining which of said plurality of ESTs are complementary to said given nucleic acid.

* * * * *